United States Patent
Matoba et al.

(10) Patent No.: US 11,921,045 B2
(45) Date of Patent: Mar. 5, 2024

(54) HOLOGRAPHIC THREE-DIMENSIONAL MULTI-SPOT LIGHT STIMULATION DEVICE AND METHOD

(71) Applicant: NATIONAL UNIVERSITY CORPORATION KOBE UNIVERSITY, Kobe (JP)

(72) Inventors: Osamu Matoba, Hyogo (JP); Xiangyu Quan, Hyogo (JP); Hiroaki Wake, Hyogo (JP)

(73) Assignee: National University Corporation Kobe University, Kobe (JP)

( * ) Notice: Subject to any disclaimer, the term of this patent is extended or adjusted under 35 U.S.C. 154(b) by 465 days.

(21) Appl. No.: 17/258,849

(22) PCT Filed: Jul. 9, 2019

(86) PCT No.: PCT/JP2019/027232
§ 371 (c)(1),
(2) Date: Jan. 8, 2021

(87) PCT Pub. No.: WO2020/013208
PCT Pub. Date: Jan. 16, 2020

(65) Prior Publication Data
US 2021/0293714 A1    Sep. 23, 2021

(30) Foreign Application Priority Data
Jul. 9, 2018  (JP) .................. 2018-130309

(51) Int. Cl.
*G01N 21/64* (2006.01)
*C12Q 1/02* (2006.01)
(Continued)

(52) U.S. Cl.
CPC .......... *G01N 21/6458* (2013.01); *C12Q 1/02* (2013.01); *G01B 9/021* (2013.01);
(Continued)

(58) Field of Classification Search
CPC .................................................. G01N 21/6458
See application file for complete search history.

(56) References Cited

U.S. PATENT DOCUMENTS

| 7,009,700 B2* | 3/2006 | Dubois | G02B 21/16 |
| | | | 359/22 |
| 8,848,199 B2* | 9/2014 | Choi | G01N 21/45 |
| | | | 356/497 |

(Continued)

FOREIGN PATENT DOCUMENTS

| JP | 2015-219501 A | 12/2015 |
| JP | 2015-219502 A | 12/2015 |

(Continued)

OTHER PUBLICATIONS

WO 2016/163560 Translation. (Year: 2016).*

(Continued)

*Primary Examiner* — David P Porta
*Assistant Examiner* — Djura Malevic
(74) *Attorney, Agent, or Firm* — Ogilvie Law Firm

(57) ABSTRACT

A holographic three-dimensional multi-spot light stimulation device is provided with: a three-dimensional imaging holographic optical system A which employs fluorescent exciting light to acquire three-dimensional fluorescence distribution information resulting from fluorescent signal light from a plurality of stimulation target objects; and a three-dimensional light stimulation holographic optical system B which employs a light stimulation hologram generated on the basis of the acquired three-dimensional fluorescence distribution information to form a plurality of light spots in space, to impart stimulation simultaneously to the plurality of stimulation target objects. Furthermore, the three-dimensional light stimulation holographic optical system B is provided with a spatial light phase modulating element 22 and a control unit 25, wherein the control unit 25 generates (Continued)

the light stimulation hologram by controlling the spatial light phase modulating element 22 on the basis of the three-dimensional fluorescence distribution information.

18 Claims, 17 Drawing Sheets

(51) Int. Cl.
| | |
|---|---|
| *G01B 9/021* | (2006.01) |
| *G02B 5/32* | (2006.01) |
| *G02B 21/06* | (2006.01) |
| *G02B 21/16* | (2006.01) |
| *G03H 1/00* | (2006.01) |
| *G03H 1/04* | (2006.01) |

(52) U.S. Cl.
CPC ........... *G01N 21/6402* (2013.01); *G02B 5/32* (2013.01); *G02B 21/06* (2013.01); *G02B 21/16* (2013.01); *G03H 1/0005* (2013.01); *G03H 1/0443* (2013.01); *G01N 2201/06113* (2013.01); *G03H 2001/005* (2013.01); *G03H 2001/0447* (2013.01); *G03H 2222/40* (2013.01)

(56) References Cited

U.S. PATENT DOCUMENTS

| | | | | |
|---|---|---|---|---|
| 9,546,952 | B2* | 1/2017 | Choi | G01N 21/51 |
| 10,568,516 | B2* | 2/2020 | Yang | A61B 5/4064 |
| 10,712,270 | B2* | 7/2020 | Matoba | G03H 1/0005 |
| 11,573,392 | B2* | 2/2023 | Yamane | G02B 7/04 |
| 2004/0156098 | A1* | 8/2004 | Dubois | G01N 21/6458 |
| | | | | 359/368 |
| 2005/0112759 | A1* | 5/2005 | Radisic | C12N 5/0658 |
| | | | | 435/366 |
| 2006/0011812 | A1* | 1/2006 | Wolleschensky .. | G01N 21/6458 |
| | | | | 250/208.1 |
| 2006/0012869 | A1* | 1/2006 | Wolleschensky .... | G02B 21/248 |
| | | | | 359/368 |
| 2006/0132799 | A1* | 6/2006 | Dubois | G02B 21/16 |
| | | | | 356/512 |
| 2007/0171519 | A1* | 7/2007 | Wolleschensky .. | G01N 21/6458 |
| | | | | 359/385 |
| 2008/0018966 | A1* | 1/2008 | Dubois | G01B 9/021 |
| | | | | 359/9 |
| 2009/0268511 | A1* | 10/2009 | Birge | G11C 13/04 |
| | | | | 365/151 |
| 2010/0330578 | A1* | 12/2010 | Duhr | C12Q 1/6813 |
| | | | | 422/82.08 |
| 2011/0249866 | A1* | 10/2011 | Piestun | G06T 7/77 |
| | | | | 382/103 |
| 2012/0287244 | A1* | 11/2012 | Bennett | G02B 21/16 |
| | | | | 348/46 |
| 2014/0313315 | A1* | 10/2014 | Shoham | G02B 21/0032 |
| | | | | 359/558 |
| 2016/0231575 | A1 | 8/2016 | Shoham et al. | |
| 2016/0377546 | A1* | 12/2016 | Ragan | G01N 21/6458 |
| | | | | 250/459.1 |
| 2018/0177401 | A1* | 6/2018 | Yang | G01N 21/6458 |
| 2019/0250104 | A1* | 8/2019 | Matoba | G03H 1/0005 |
| 2021/0293714 | A1* | 9/2021 | Matoba | G02B 21/06 |

FOREIGN PATENT DOCUMENTS

| | | |
|---|---|---|
| WO | 2016/163560 A1 | 10/2016 |
| WO | 2018070451 A1 | 4/2018 |

OTHER PUBLICATIONS

Oscar Hernandez, et al., "Three-dimensional spatiotemporal focusing of holographic patterns", retrieved via <<https://www.nature.com/articles/ncomms11928>>, 2016, 11 pages.

Morad Zahid, et al., "Holographic Photolysis for Multiple Cell Stimulation in Mouse Hippocampal Slices", retrieved from <<https://journals.plos.org/plosone/article?id=10.1371/journal.pone.0009431>>, 2010, 13 pages.

Xiangyu Quan, et al., "Three-dimensional stimulation and imaging-based functional optical microscopy of biological cells", Optics Letters, vol. 43, No. 21, Nov. 1, 2018, pp. 5447-5480.

European Search Report, PCT/JP2019027232, dated Mar. 4, 2022, 11 pages.

* cited by examiner

HOLOGRAPHIC THREE-DIMENSIONAL MULTI-SPOT LIGHT STIMULATION DEVICE AND METHOD

RELATED APPLICATIONS

The present application claims priority to, and incorporates by reference the entirety of, PCT application no. PCT/JP2019/027232 filed 9 Jul. 2019 and Japanese application no. 2018-130309 filed 9 Jul. 2018.

TECHNICAL FIELD

This invention relates to a technology that applies light stimulation simultaneously to many objects three-dimensionally positioned, based on three-dimensional fluorescence distribution information. Using three-dimensional fluorescence distribution information, a status of an object is observed after light stimulation is applied.

BACKGROUND ART

In recent years, optogenetics has been studied, in which the activity of cells expressing photoactivated proteins and physiological functions such as signal transduction are photomanipulated by operating optogenetically to reorganize neural circuits and elucidate vital functions. Microscopes are expected to function as operational tools in addition to being tools for measurement and observation in biological applications. For example, it is expected that by using light pulses of visible light, light-stimulated proteins in cell membranes will be stimulated to achieve fast and accurate time control of cell action potential patterns and realize on/off switching of neural circuits.

The technology of performing programmable photostimulation on cells distributed three-dimensionally at the same time or with a time lag is a technology that dramatically advances the research level of optogenetics research. For this purpose, it is necessary to develop a technique for sensing the three-dimensional position of a cell at high speed and generating a plurality of light spots based on the information.

On the other hand, as three-dimensional imaging of cells distributed three-dimensionally, for example, a technique is known which introduces a fluorescent molecule to specific DNA in cell nuclei and measures changes in living cells using a fluorescence microscope. By visualizing interactions of nuclei and proteins in cells stained with fluorescent molecules, it is possible to observe the cell activity expressing photoactivated proteins.

In addition, as a tool that enables measurement of changes in cell activity and simultaneous measurement of multiple cells with different depth positions, a digital holographic microscope is known. In a digital holographic microscope, three-dimensional information is acquired as hologram information, and light wave information of an object with respect to a depth position is reconstructed by performing a back propagation calculation of the light wave in a computer. Therefore, three-dimensional observation of living cells is possible without the need for special fluorescent staining, the focal position can be arbitrarily changed by computer reconstruction, and quantitative phase measurement is possible. For this reason, even in an observation of three-dimensionally dynamic cells, it is possible to obtain a focused reconstructed image automatically by reconstruction calculations.

When observing cells stained with fluorescent molecules using a digital holographic microscope, since fluorescence is incoherent light that does not easily interfere, using a spatial light modulator to create holograms from incoherent light, a Fluorescence Digital Holographic Microscope (FDHM) is known. (for example, refer to Patent Documents 1 and 2)

The apparatus disclosed in Patent Document 1 is for observing light with low coherence (for example, fluorescent light etc.), and by employing a spatial light modulator, the object light including the first component light and the second component light with polarizing directions thereof different to each other is made to have the wave front shape of the first component light and the wave front shape of the second component light which are different than each other, generating a distribution that changes spatially and periodically, and a hologram is formed by making the first component light and the second component light interfere. As a result, it is possible to obtain a reconstructed image of the subject from a hologram recorded in one imaging using low-coherence light passing through a single light path.

In addition, the inventors combine a fluorescent digital holographic microscope and a phase three-dimensional image detection digital holographic microscope to simultaneously measure the three-dimensional fluorescence image and the three-dimensional phase image, and propose a multimodal digital holographic microscope capable of observing various information including not only the three-dimensional fluorescence image but also the three-dimensional phase image. (refer to Patent Document 2)

Further, a light stimulator that stimulates a biological object by light irradiation thereon is known. (for example, refer to Patent Document 3) The light stimulator disclosed in Patent Document 3, in order to restrain problems such as reduction of the focusing intensity of the irradiation light and suppression of the spread of the focused shape inside the biological object, acquires information regarding the shape with a difference of refractive index in the biological object, generates aberration-corrected hologram data for correcting aberrations caused by the shape with a difference in refractive index, and a hologram based on the created aberration-corrected hologram data is presented. Then, the light emitted to the biological object is modulated using the spatial light modulator.

PRIOR ART

Patent Documents

[Patent Document 1] JP 2015-1726 A
[Patent Document 2] JP 2016-163560 A1
[Patent Document 3] JP 2015-219502 A

OUTLINE OF THE INVENTION

Problems to be Solved by the Invention

Conventionally, optical manipulation processes in optogenetics have been implemented by optical fiber technology or optical windows above the target area.

However, one of the problems is that the cells to be stimulated exist in a wide range and that the optical system for imaging is two-dimensional illumination, which limits the excitation of cells to be limited to locally specified cells. In order to further understand nerve cells, it is necessary to have an accuracy of the millisecond order and to be able to illuminate and stimulate cells by 3D multi-spots. Therefore, as described above, there is a need for a technique that performs programmable photic stimulation of a plurality of cells distributed three-dimensionally at the same time or with a time lag, and therefore, a device is demanded that senses and generates a plurality of light spots allowing the three-dimensional position of the cells to be moved at high speed.

In view of this situation, an object of the present invention is to provide a holographic three-dimensional multi-spot light stimulation device capable of rapidly sensing the three-dimensional positions of a plurality of target objects, and imparting light stimulation simultaneously to the plurality of target objects, which are positioned three-dimensionally, on the basis of three-dimensional fluorescence distribution information that has been obtained.

Means to Solve the Objects

In order to achieve the above object, the holographic three-dimensional multi-spot light stimulator of the present invention is provided with: a three-dimensional imaging holographic optical system which employs fluorescent exciting light to acquire three-dimensional fluorescence distribution information resulting from fluorescent signal light from a plurality of stimulation target objects; and a three-dimensional light stimulation holographic optical system which employs a light stimulation hologram generated on the basis of the acquired three-dimensional fluorescence distribution information to form a plurality of light spots in space, to impart stimulation simultaneously to the plurality of stimulation target objects.

According to the above configuration, the three-dimensional positions of a plurality of objects are sensed at high speed, and light stimulation is simultaneously applied to the plurality of objects located three-dimensionally based on the obtained three-dimensional fluorescence distribution information.

The three-dimensional imaging holographic optical system is a system for three-dimensional observation of the fluorescence distribution of multiple objects to be stimulated. The three-dimensional light stimulation holographic optical system is a system that gives a stimulus to a plurality of stimulus objects located in a three-dimensional space. Both systems are realized by holographic technology.

Stimulation for the stimulation object is possible only when the three-dimensional positions of a plurality of objects can be sensed at high speed and the three-dimensional fluorescence distribution information can be acquired. How to acquire the three-dimensional fluorescence distribution information of the stimulus target and to instantly observe the state change of the stimulus target after the stimulus is executed will be described in detail in an Embodiment described later.

Note that, both a laser light having a coherent property and a light such as an LED having a partial coherent property can be used as the fluorescence excitation light. It is also possible to use a near-infrared light laser, which has better permeability of living tissue than visible light or an ultraviolet light laser, as the fluorescence excitation light to generate excitation by two-photon absorption on the object to be stimulated.

In the holographic three-dimensional multi-spot light stimulation device of the present invention, the three-dimensional light stimulation holographic optical system includes a first spatial light modulator and a control unit, and the control unit controls the first spatial light modulator based on the three-dimensional fluorescence distribution information to obtain light and generate a stimulating hologram.

A spatial light modulator (SLM) is an element in which the state of liquid crystal molecules changes depending on the voltage, causing a phase delay or modulation of the amplitude. The spatial light modulator can produce different effects on the polarization state of the incident photoelectric field depending on the orientation of the liquid crystal molecules, and when it acts as an ordinary ray with respect to linearly polarized light in a certain direction, it also acts as an abnormal ray against linearly polarized light perpendicular to it. Therefore, it is possible to realize a bifocal lens having a polarization dependence that acts only in a specific linear polarization direction. As for the fluorescent signal light, two diffracted lights are generated by the double lens realized by the spatial light modulator, and the two diffracted lights are both the same polarized light and self-interference occurs.

Further, the control unit identifies the positions of a plurality of stimulation objects to be light-stimulated based on the three-dimensional fluorescence distribution information, and calculates a hologram for photic stimulation for forming a plurality of light spots at specific positions simultaneously and generates a hologram for photic stimulation by controlling the first spatial light modulator. The first spatial light modulator is either a phase modulation type spatial light modulator or an amplitude modulation type spatial light modulator. An amplitude modulation type spatial light modulator may be useable as a phase modulator. Here, the spatial light modulator is arranged at the position of the Fourier transform or the image formation position of the objective lens with respect to the focal plane of the objective lens.

In a holographic three-dimensional multi-spot light stimulation device of the present invention, it is preferable that the three-dimensional light stimulation holographic optical system uses a plurality of wavelengths of the modulated light by the light stimulation hologram at the same time, or by switching the wavelengths. Depending on the characteristics of the object to be stimulated, the stimulus can be applied by using a plurality of wavelengths of the modulated light by the light stimulating hologram, or the stimulus can be applied by switching the wavelength. By using a plurality of wavelengths of modulated light, it is possible to light-stimulate a plurality of objects to be stimulated at the same time in a three-dimensional space using a plurality of wavelengths. For example, when the stimulation target is excited by using both blue wavelength light and green wavelength light, or when the stimulation target is excited by switching between blue wavelength light and green wavelength light. It is also possible to deal with the case where the state of the object to be stimulated is controlled by switching the wavelength.

In particular, the modulated light by the light stimulation hologram may be fluorescence excitation light or state control light for controlling the state of the stimulation object. By using the modulated light produced by the photic stimulation hologram as the fluorescence excitation light, it is possible to observe while tracking a specific stimulation object. Further, by using the modulated light by the light stimulation hologram as the state control light, the technique of the present invention can be used for controlling the on/off of cells in the field of optogenetics, for example.

It is preferable that both the three-dimensional imaging holographic optical system and the three-dimensional light stimulation holographic optical system are reflective.

In order to give light stimulation to living cells in the living body, both are made into a reflective (epi-illuminated) optical system. When light stimulation is applied to cells outside the living body, and when the three-dimensional imaging holographic optical system is a transmissive type instead of a reflective type (epi-illumination type), the fluorescence signal light to be observed is weak, so a dichroic mirror that sufficiently cuts the fluorescence excitation light and allows only the fluorescence signal light to pass through and/or a bandpass filter that allows a specific wavelength and phase measurement to pass through is employed.

In a holographic three-dimensional multi-spot light stimulation device of the present invention, the three-dimensional imaging holographic optical system is equipped with a second spatial light modulator, a polarization-dependent bifocal lens, a polarization-dependent bifocal lens with a diffraction grating, or a volumetric holographic optical element having the same function and three-dimensional fluorescence distribution information is acquired by self-interfering the fluorescence signal light.

In the three-dimensional light stimulation holographic optical system, it turns out that a spatial light modulator is used due to the necessity of rewriting the hologram, but the three-dimensional imaging holographic optical system is not limited to the spatial light modulator; a double focus lens having polarization dependence and a double focus lens with a grating having polarization dependence and a fixed volumetric holographic optical device can also be used.

Further, in the holographic three-dimensional multi-spot light stimulation device of the present invention, the three-dimensional imaging holographic optical system may acquire three-dimensional fluorescence distribution information by self-interfering the fluorescence signal light using a bifocal Fresnel lens having a sub-wavelength periodic structure (SPFL). The sub-wavelength periodic structure is a structure for exhibiting polarization dependence, which is diffracted by the polarization state of the light wave by the sub-wavelength periodic structure that is a diffraction grating structure having a period shorter than the wavelength of the light. Further, a Fresnel lens is a lens obtained by folding a normal lens at a wavelength of light to reduce the thickness, and has a saw-like cross section and a shape like an array of prisms. The bifocal Fresnel lens has a function of dividing one beam light into two parts, diffracting them, and focusing them at different places. Further, the three-dimensional imaging holographic optical system may acquire three-dimensional fluorescence distribution information by self-interfering the fluorescence signal light by using a volumetric holographic optical element having both a bifocal lens and a diffraction grating.

In the three-dimensional imaging holographic optical system, a plurality of wavelengths of the fluorescence excitation light may be used, or the wavelengths used may be switched. A plurality of wavelengths of fluorescence excitation light are prepared or switched according to the fluorescence characteristics of the object. By switching the wavelength of the fluorescence excitation light used according to the type of the fluorescence staining reagent, it is possible to select a target cell and measure changes in the cell state such as division and shape change.

It is preferable that the holographic three-dimensional multi-spot light stimulation device of the present invention further includes a holographic optical system for phase imaging that acquires a phase three-dimensional image by interference light obtained by superimposing object light passing through an object to be stimulated and reference light not passing through.

By further providing a holographic optical system for phase imaging, for example, when observing cells, the spatiotemporal information of the cell nucleus is acquired by the three-dimensional fluorescence image, and the spatiotemporal structure of the cell nucleus and the cell wall is simultaneously acquired by the three-dimensional phase image. This makes it possible to photograph simultaneously and at a high speed a three-dimensional fluorescence image and a three-dimensional phase image.

The three-dimensional imaging holographic optical system and the imaging sensor of the holographic optical system for phase imaging may be shared, and the fluorescence three-dimensional image and the phase three-dimensional image may be simultaneously acquired as holograms. In this case, the three-dimensional fluorescence image of the equal tilt-angle hologram due to off-axis interference and the three-dimensional phase image of the equal tilt-angle hologram are separated in the spatial frequency plane, and the object light and the fluorescence signal light are reconstructed from the respective interference intensity distributions.

In the holographic three-dimensional multi-spot light stimulation device of the present invention, when the object to be stimulated is a cell group, a plurality of light spots can be spatially formed using a light-stimulating hologram to stimulate a plurality of cells simultaneously and the state of the cell group after the stimulus is applied can be observed three-dimensionally. When the object to be thermally stimulated is a cell group, excitation by 2-photon absorption can be generated for a group of cells located at a depth of several hundred μm from the tissue surface of the sample by using a near-infrared light laser, which has better transmission in biological tissue than visible light or ultraviolet light laser, as fluorescence excitation light. It is possible to reduce the damage to the cell group, promote the activity of nerve cells occurring in the brain of a living animal, and observe the state of activity.

In a holographic three-dimensional multi-spot light stimulation device of the present invention, the three-dimensional imaging holographic optical system images a three-dimensional fluorescence distribution using an image sensor of a pixel matrix. Alternatively, a single detector may be used to modulate the spatial pattern of the fluorescent signal with a DMD to obtain the light energy of the modulated fluorescent signal. A digital mirror device (DMD) is an optical element that uses a display element in which a large number of micromirrors are arranged in a plane to turn on at least one micromirror and partially transmit fluorescence excitation light or fluorescence signal light. A system can be constructed that can acquire holograms for weak fluorescence signals by inserting a display element such as a DMD that can freely set the modulation pattern in the middle of the optical path between the light source of fluorescence excitation light or fluorescence signal light and the detector. Thereby, at the time of application to a living tissue, by suppressing the light energy irradiating the living tissue, it is possible to acquire the fluorescent signal light without damaging the living tissue.

Next, a holographic three-dimensional multi-spot light stimulation method of the present invention will be described.

The holographic three-dimensional multi-spot light stimulation method of the present invention includes the following steps 1) to 6).

1) A step of irradiating a plurality of stimulation objects with fluorescence excitation light.
2) A step of acquiring hologram information of a three-dimensional fluorescence distribution due to the fluorescence signal light of the object to be stimulated.

3) A step of observing the state of the object to be stimulated by reconstructing the acquired hologram information of the three-dimensional fluorescence distribution with a computer.
4) A step of generating a hologram for light stimulation based on the acquired hologram information of the three-dimensional fluorescence distribution.
5) A step of spatially forming a plurality of light spots using a hologram for light stimulation and simultaneously applying light stimulation to a plurality of stimulation objects.
6) A step of observing the state of a stimulus object after application of stimulus by reconstructing hologram information of a three-dimensional fluorescence distribution by fluorescent signal light accompanied by light stimulus.

The step of generating the hologram for light stimulation in 4) above includes a step of specifying the positions of a plurality of objects to be stimulated by light based on the hologram information of the three-dimensional fluorescence distribution, a step of calculating a hologram for light stimulation for forming a plurality of light spots simultaneously at the specified positions and a step of controlling a spatial light modulator and generating a light stimulation hologram.

In the step of simultaneously stimulating the stimulus object in 5) above, not only the single wavelength modulated light by the light stimulus hologram is used, but also the modulation by the light stimulus hologram is performed according to the characteristics of the stimulus object, or it is possible to use a plurality of wavelengths of light at the same time, or to switch the wavelengths. When the light modulated by the light stimulus hologram is fluorescence excitation light, the fluorescence signal light appears with the application of the light stimulus, so that the state of the stimulus object immediately after the stimulus is applied can be observed. Further, in the case of the state control light in which the light modulated by the light stimulation hologram controls the state of the stimulated object, it can be used for controlling the on/off of cells in the field of optogenetics, for example.

Effects of the Invention

According to the present invention, there are effects such that three-dimensional positions of a plurality of objects are sensed at high speed, and light stimulation is simultaneously applied to a plurality of objects located three-dimensionally based on the obtained three-dimensional fluorescence distribution information. Further, according to the present invention, there is also an effect that the state of the object after the application of the light stimulus can be observed three-dimensionally by the three-dimensional fluorescence distribution information of the fluorescence signal light accompanying the light stimulus.

BRIEF DESCRIPTION OF THE DRAWINGS

FIG. 16 shows an explanatory diagram (2) of experimental results using fluorescent beads.
FIG. 16 shows an explanatory diagram (3) of experimental results using fluorescent beads.

MODE FOR CARRYING OUT THE INVENTION

Embodiments of the present invention will be described in detail below with reference to the drawings. The present invention is not limited to the following embodiments and examples shown in the figures, and the present invention can be variously changed in design.

Embodiment 1

Figure 1:
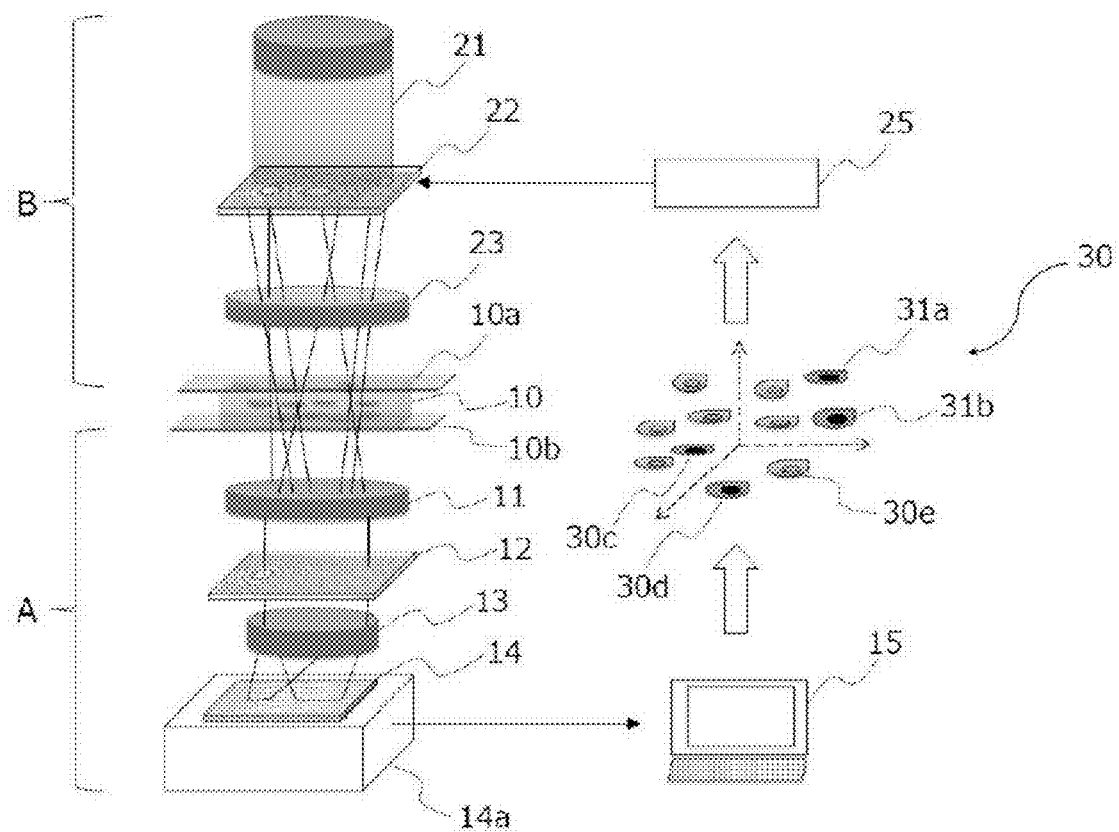
FIG. 1 shows a schematic diagram of a holographic three-dimensional multi-spot light stimulation device in Embodiment 1.

FIG. 1 shows a schematic diagram of an Embodiment of the holographic three-dimensional multi-spot light stimulation device. As shown in FIG. 1, the holographic three-dimensional multi-spot light stimulation device includes a three-dimensional imaging holographic optical system A and a three-dimensional light stimulation holographic optical system B.

The three-dimensional imaging holographic optical system A is an optical system that handles the fluorescence signal light of a stimulation object 10 by the laser light (fluorescence excitation light) emitted from a laser light source 21. In the optical system A, the fluorescent signal light of the stimulation object 10 is formed into a shape close to parallel light by an objective lens 11 and is incident on a phase modulation type spatial light modulator (hereinafter, simply referred to as "spatial light phase modulator") 12. The fluorescent signal light transmitted through the spatial light phase modulator 12 passes through a tube lens 13 and reaches an image sensor 14. Here, the spatial light phase modulator 12 functions as a bifocal lens on which a diffraction grating is superimposed, so that the image sensor 14 can acquire a fluorescence three-dimensional image by self-interference of the fluorescence signal light. Since the fluorescence signal light self-interferes, the obtained three-dimensional fluorescence image becomes a hologram of an interference fringe pattern having an equal inclination angle. An arithmetic unit 15 calculates a three-dimensional map 30 which is three-dimensional fluorescence distribution information of a plurality of the stimulation objects 10 by using a hologram of an interference fringe pattern having an equal inclination angle.

On the other hand, in the three-dimensional light stimulation holographic optical system B, the laser light (parallel light) emitted from a laser light source 21 is incident on a spatial light phase modulator 22, and the transmitted light is irradiated to the stimulation object 10 through an objective lens 23. The spatial light phase modulator 22 is controlled by a control unit 25 so that a pattern of the light stimulation hologram is formed based on the three-dimensional map 30 calculated by the three-dimensional imaging holographic optical system A. The laser beam transmitted through the spatial light phase modulator 22 on which the pattern of the light stimulation hologram is formed spatially forms a plurality of light spots by self-interference. Therefore, the laser beam is concentrated on the stimulation target object 10 by the objective lens 23, and light spots are formed at the three-dimensional positions of the plurality of stimulation objects 10 to simultaneously apply stimulation to the plurality of stimulation target objects 10.

The stimulation object 10 is sandwiched between a cover glass 10a and a glass plate 10b and attached to a sample stage (not shown). The stimulation object 10 may be housed in a glass container without being sandwiched between the plate-shaped glasses. A material other than glass may be used as long as it is a material that transmits laser light.

The stimulation object 10 is, for example, a cell group of a living body, and three-dimensional fluorescence distribution information of a plurality of cells can be acquired as individual fluorescence positions 31a to 31e of the three-dimensional map 30 by the three-dimensional imaging holographic optical system A. Then, a plurality of light spots can be spatially formed by the three-dimensional light stimulation holographic optical system B, and stimulation can be simultaneously applied to a plurality of cells which are the stimulation object 10.

As described above, the three-dimensional multi-spot light stimulator of the present invention is configured with 2 holographic technologies such as a three-dimensional imaging holographic optical system A that performs three-dimensional observation of the fluorescence distribution of the stimulus object and a three-dimensional light stimulation holographic optical system B that provides stimulus to the stimulus object located in the three-dimensional space. In order to give an accurate stimulus to the targeted stimulus target, a three-dimensional map which is three-dimensional fluorescence distribution information of the stimulus target is calculated. In addition, after the stimulus is applied to the stimulus object, the dynamic change (a change in the three-dimensional position) of the stimulus object is observed in real time, and the three-dimensional map is calculated anew in order to give the next stimulus. It is necessary to repeat observation and stimulation in this way. If the object to be stimulated is a group of cells in a living body, a stimulation on the order of milliseconds is applied, so that the observation is at the same speed, namely, the observation at a high speed on the order of milliseconds should be performed. In order to realize high-speed 3D observation, digital holographic technology using off-axis incoherent light of a common path is adopted.

In the following, a digital holographic technique using common optical path type off-axis incoherent light will be described, along with how to create a three-dimensional map of the stimulus object and stimulate the stimulus object, and how to observe the state change of the stimulus object in real time after the stimulus is applied, with reference to FIG. 2.

First, how to create a 3D map of the stimulus object will be explained. It is assumed that the object to be stimulated has the property of being fluorescent when irradiated by the excitation light. When the stimulation target is irradiated with fluorescence excitation light, the stimulation target emits fluorescence signal light. As shown in A of FIG. 2, the fluorescence signal light emitted by the fluorescent object of a pseudo point source σ ($x_s$, $y_s$, $z_s$) passes through the objective lens 11, the spatial light phase modulator 12, and the tube lens 13. Finally, it reaches the image sensor 14. Although fluorescent excitation light of reflected light or transmitted light may be mixed with fluorescence signal light, a dichroic mirror (not shown) is used to reflect light of a specific wavelength and transmit light of other wavelengths, by doing so, for example, the fluorescence excitation light can be sufficiently attenuated and the fluorescence signal light can be emphasized. When the object to be stimulated is a cell group or the like, a plurality of fluorescent objects exist, and these many fluorescent objects can be regarded as superposed pseudo point light sources in a sample space (for example, a sample space housed in a glass container).

The spatial light phase modulator 12 has a polarization dependence and has a function of a bifocal lens on which a diffraction grating is superimposed. Due to the function of the bifocal lens, two diffracted waves are generated from one fluorescence signal light, and these fluorescence signal lights self-interfere with each other, so that the image sensor 14 can acquire a three-dimensional fluorescence image. Since the fluorescence signal light is tilted in the traveling direction due to diffraction and self-interferes, the fluorescence three-dimensional image becomes a hologram having an interference fringe pattern with an equal inclination angle. Alternatively, due to the polarization dependence, interference between unmodulated light and modulated light can also be used. At this time, the polarized light of the two lights is aligned and interfered with each other by using a polarizing plate.

In the spatial light phase modulator 12 having a polarization dependence, light having a specific polarization direction is passed and focused on the optical axis, and light having a different polarization direction is blocked. Further, when the spatial light phase modulator 12 has the function of a double focus lens on which a diffraction grating is superimposed, the light incident parallel to the optical axis is not focused on the optical axis, but is deviated from the optical axis by the diffraction grating. As a result of the interference of light waves diffracted by different slits, the incident light propagates strongly only in a specific direction. When there is a difference in optical path length that is an integral multiple of the wavelength of light between light waves diffracted by adjacent slits, strong diffracted light is generated. Since light with a specific polarization direction is passed due to polarization dependence, the polarization direction passing through the slit of the diffraction grating is matched with the specific polarization direction, diffraction is performed by the diffraction grating, and the focusing point deviates from the optical axis. Here, the opening of a shutter (not shown) is not provided on the optical axis so as to block the light collected on the optical axis. The light to be blocked includes light having a polarization direction different from that of the diffraction grating, surface-reflected light by an optical element, randomly polarized noise light and such.

The fluorescent signal light emitted from the pseudo point source $\sigma$ ($x_s$, $y_s$, $z_s$) has a quadratic phase distribution shown in the following equation (1) on the one-dimensional axis of $x_0$ in the plane of the spatial light phase modulator 12. Here, $r_0$ is the radius of the fluorescence signal light, and is represented by $r_0 = f_{OL}^2/z_s$. $f_{OL}$ is the focal length of the objective lens 11, and $\lambda$ is the center wavelength of the fluorescence signal light. The spatial light phase modulator 12 (hereinafter abbreviated as SLM1) possesses a phase modulation function $u_{SLM1}$ represented by the following equation (2).

[Equation 1]
$$u_{Int}(x_0) = \exp\left(\frac{i\pi x_0^2}{r_0 \lambda}\right) \exp\left(i 2\pi x_0 \frac{x_s}{f_{0L}\lambda}\right) \quad (1)$$

[Equation 2]
$$u_{SLM1}(x_0) = \exp\left(-\frac{i\pi}{f_{SLM1}\lambda} x_0^2\right) \exp\left(i 2\pi x_0 \frac{1}{d_h}\right) \quad (2)$$

The phase modulation function $u_{SLM1}$ is composed of a lens function having a focal length $f_{SLM1}$ and a diffraction grating function having a lattice period $d_h$. The portion of the spatial light phase modulator 12 in a polarized state parallel to the abnormal axis becomes $u_{Int} \times u_{SML1}$, and the abnormal axis remains unchanged as $u_{Int}$. The surface of the image sensor 14 corresponds to the BFP (Back Focal Plane) of the tube lens 13, and the abnormal ray $u_{ex}$ and the normal ray $u_{or}$ are represented by the following equations (3) and (4).

[Equation 3]
$$u_{ex}(x_h) = \exp\left\{\frac{i\pi}{\lambda r_1}\left(x_h - x_s M_1 - \frac{f_{Tube}}{d_h}\right)^2\right\} \quad (3)$$

$$u_{or}(x_h) = \exp\left\{\frac{i\pi}{\lambda r_2}(x_h - x_s M_2)^2\right\} \quad (4)$$

here, $r_1 = \frac{f_{Tube}^2}{f_{SLM_1}} - z_s\left(\frac{f_{Tube}}{f_{OL}}\right)^2$, $r_2 = -z_s\left(\frac{f_{Tube}}{f_{OL}}\right)^2$ $M_u = \frac{f_{Tube} - r_i}{f_{OL-z_s}} (u = 1, 2)$ Here, $f_{Tube}$ is the focal length of the tube lens 13. By providing a linear polarizing element, it becomes possible to form a hologram from these two beams. The hologram from the pseudo point source $\sigma$ ($x_s$, $y_s$, $z_s$) forms part of a Fresnel zone plate with a focal length $z_h = \pm r_1 r_2/(r_1 - r_2)$. When reconstructing a pseudo point source, it is possible to apply the reconstruction distance $z_h$ to restore the focused point.

Next, the creation of a hologram for three-dimensional light stimulation will be described. In B of FIG. 2, in the case of typical wide-field epi-radiation fluorescence imaging, the stimulating light is focused on the BFP (Back Focal Plane) of the objective lens 23 to form a collimated beam on the sample of the stimulation object. Conversely, the collimated beam on the BFP focuses on the sample plane.

When the incident wave plane $u_{in}$ has a specific phase distribution as represented by the following formula (5), the wave plane in the front focal plane (FFP) after the objective lens 23 is represented by the following formula (6).

[Equation 4]
$$u_{in}(x) = \sum_k \exp\left(\frac{-i\pi x^2}{\lambda h_k}\right) \exp\left(i 2\pi x \frac{1}{g_{xk}}\right) \quad (5)$$

[Equation 5]
$$u_{FFP}(X) = \sum_k \exp\left\{-\frac{i\pi}{\lambda H_k}\left[(X - G_{xk})^2\right]\right\} \quad (6)$$

Figure 2:
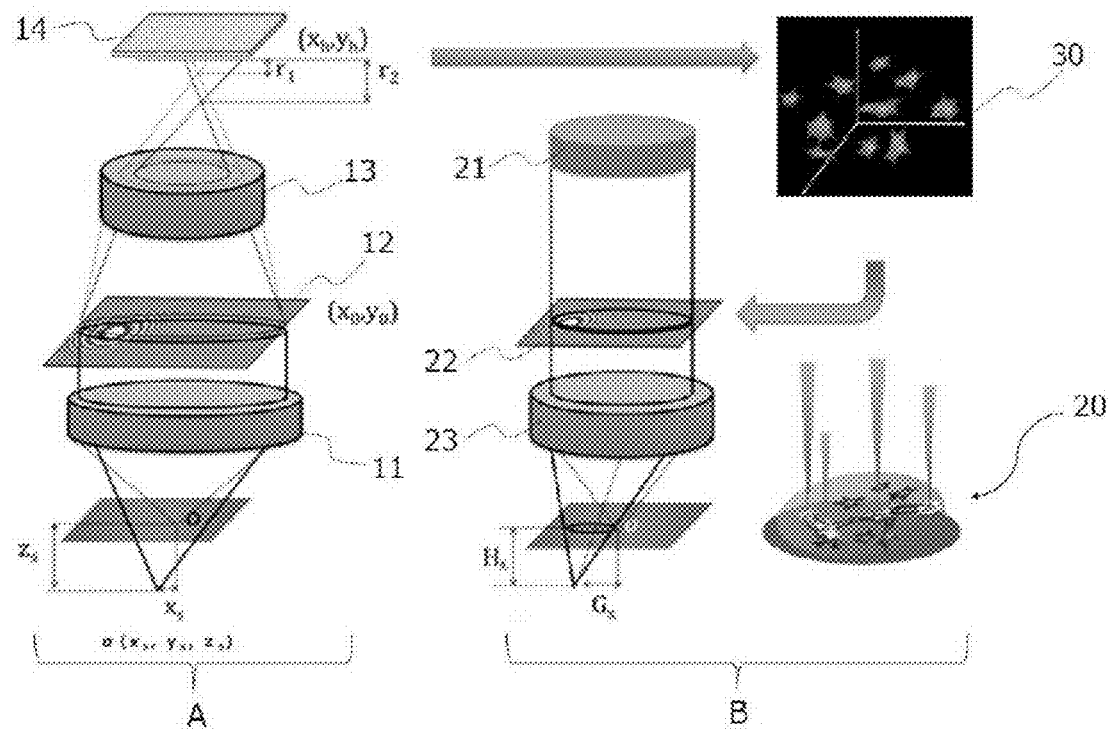
FIG. 2 shows a schematic diagram of a three-dimensional imaging holographic optical system and a three-dimensional light stimulation holographic optical system.

Here, assuming that $H_k = f_{OL}^2/h_k$ and $G_{xk} = f_{OL}\lambda/g_{xk}$ as shown in B of FIG. 2, the kth focused spot is to exist at a position in the sample space ($G_{xk}$, $G_{yk}$, $H_k$). The spatial light phase modulator 22 can modulate only the phase and modulate the collimated incident light to a desired phase distribution for each pixel.

Figure 3:
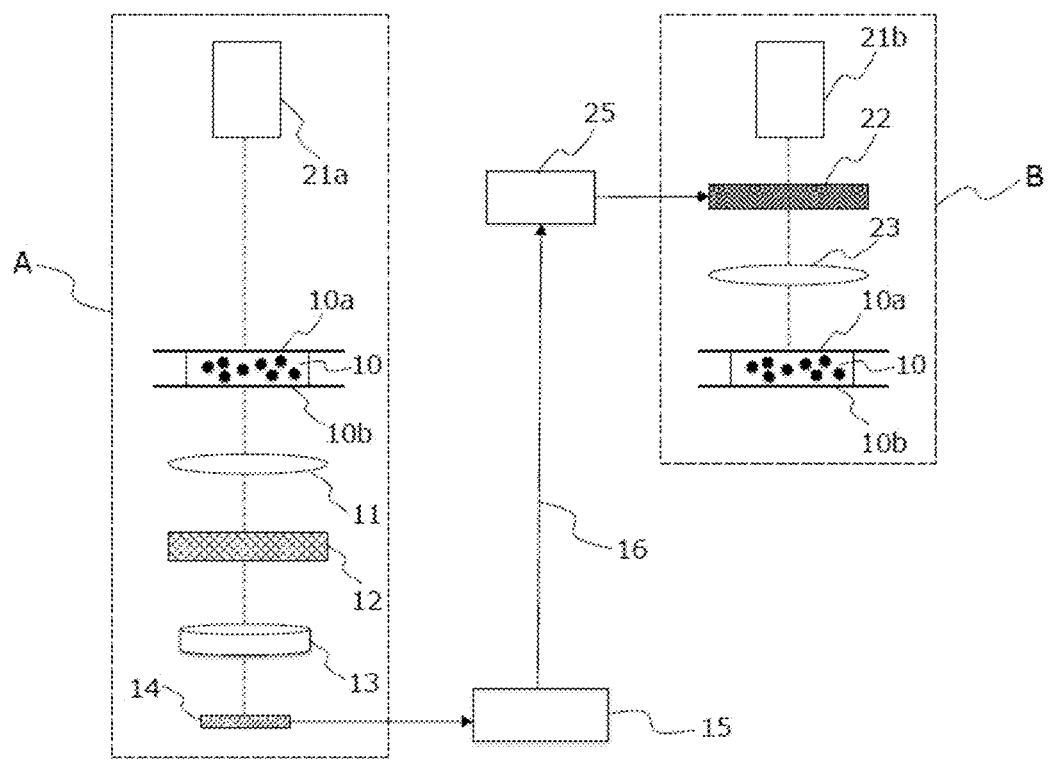
FIG. 3 shows a configuration diagram of a three-dimensional imaging holographic optical system and a three-dimensional light stimulation holographic optical system.
Figure 4:
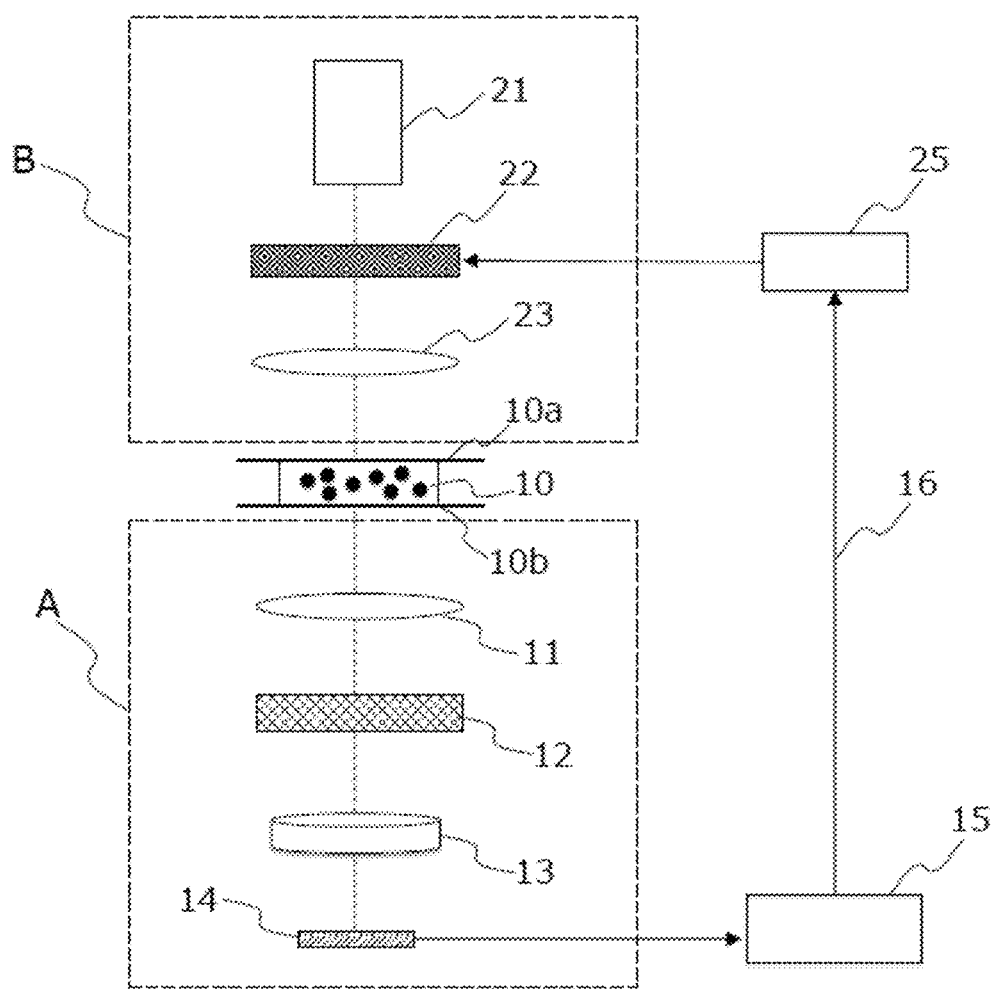
FIG. 4 shows a configuration diagram of a second holographic optical system that acquires a three-dimensional fluorescence image in Embodiment 1.

The holographic three-dimensional multi-spot light stimulation device of this Embodiment integrates the three-dimensional imaging holographic optical system A and the three-dimensional light stimulation holographic optical system B shown in FIG. 3 to form the configuration shown in FIG. 4, and makes it possible to provide light stimulation with high spatiotemporal resolution to many stimulus objects three-dimensionally based on the three-dimensional positional information.

In the three-dimensional imaging holographic optical system A, by simultaneously using or switching between multiple laser light sources according to the type of fluorescent staining reagent, the target cells are selected, the shape changes and movements are measured, and the plurality of cells distributed three-dimensionally can be photostimulated simultaneously or with a time lag.

Figure 5:
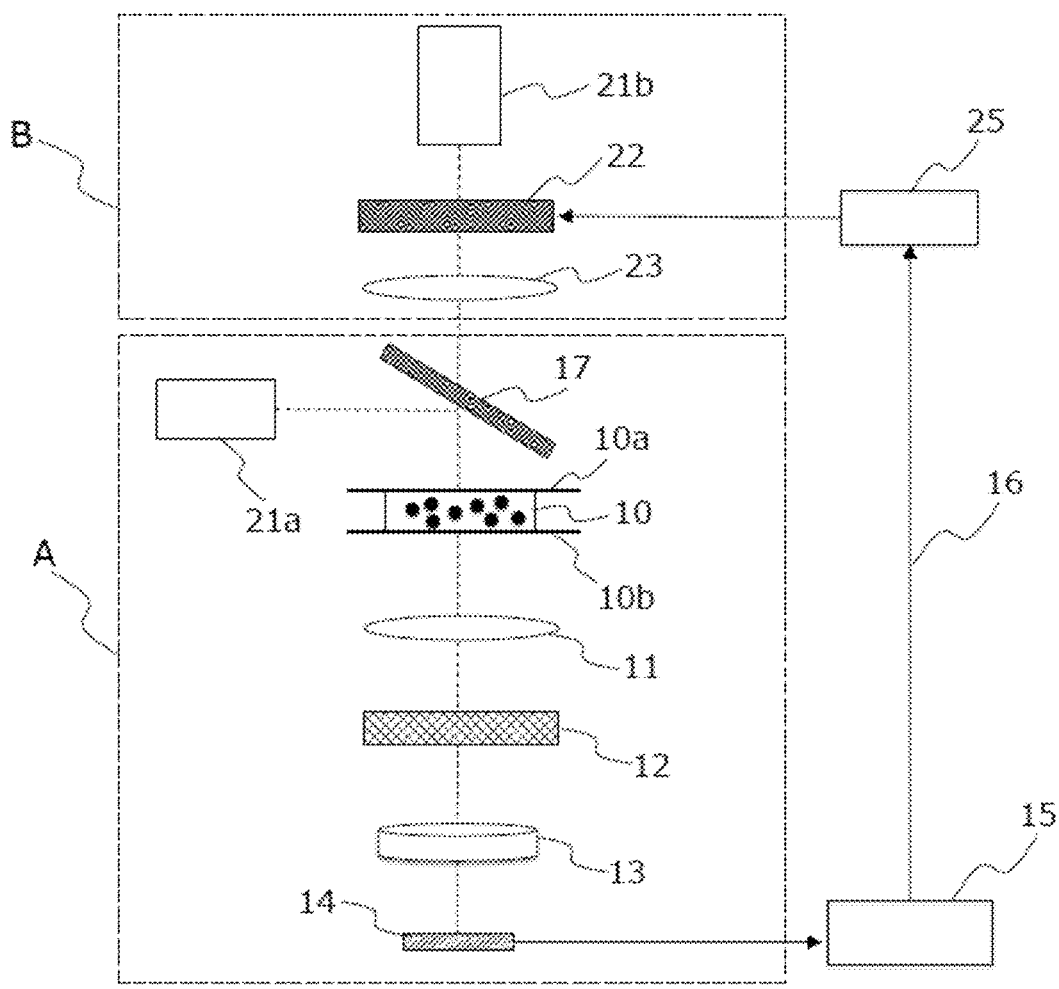
FIG. 5 shows a configuration diagram of another embodiment of the second holographic optical system that acquires a three-dimensional fluorescence image in Embodiment 1.

FIG. 5 shows a modification of the holographic three-dimensional multi-spot light stimulation device of this Embodiment, namely, a configuration using two laser light sources (21a, 21b), that are a laser light source 21a of the three-dimensional imaging holographic optical system A and a laser light source 21b of the three-dimensional light stimulation holographic optical system B. The laser light source 21a emits fluorescence excitation light, and irradiates the stimulation target 10 with a beam splitter 17. On the other hand, the laser light source 21b emits stimulation light having the same or different wavelength as the fluorescence excitation light to irradiate the stimulation target 10. The beam splitter 17 reflects the fluorescence excitation light emitted from the laser light source 21a and transmits the stimulation light emitted from the laser light source 21b. The beam splitter 17 is composed of things such as a half mirror, a dichroic mirror, and the like (the same applies to the beam splitter described later).

Embodiment 2

Figure 6:
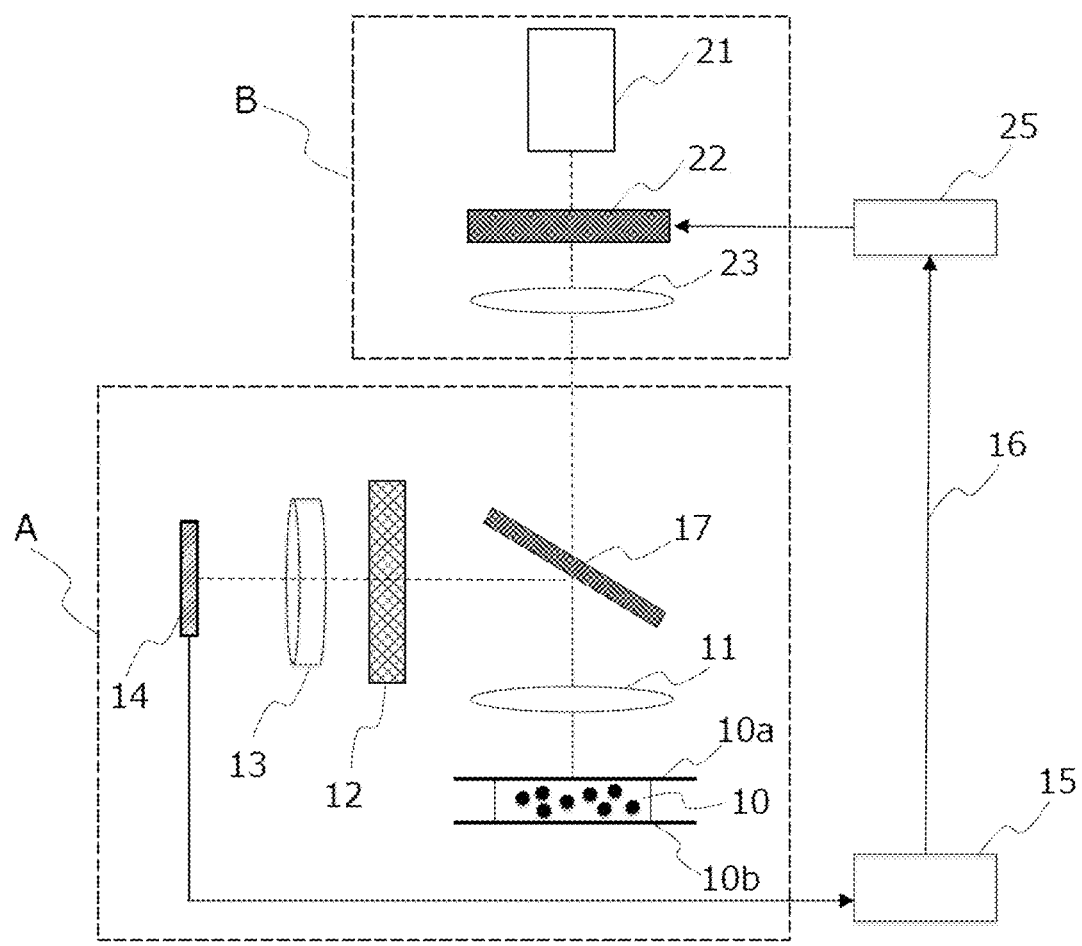
FIG. 6 shows a configuration diagram of a holographic three-dimensional multi-spot light stimulation device in Embodiment 2.

FIG. 6 shows a configuration diagram of another Embodiment of the holographic three-dimensional multi-spot light stimulation device. The holographic three-dimensional multi-spot light stimulation device shown in FIG. 6 includes a three-dimensional imaging holographic optical system A and a three-dimensional light stimulation holographic optical system B as in the device of the Embodiment 1 described above, while the three-dimensional imaging holographic optical system A does not process the fluorescence signal light on the opposite side (transmittance side) to the incident side but processes the fluorescent signal light of the stimulation target 10, which differs from the device of Embodiment 1 described above.

That is to say, in the three-dimensional imaging holographic optical system A shown in FIG. 6, the fluorescence signal light emitted by the stimulation object 10 from the fluorescence excitation light emitted by the laser light source 21 is made parallel by the objective lens 11 and reflected by the beam splitter 17 to be incident on spatial light phase modulator 12. The fluorescent signal light transmitted through the spatial light phase modulator 12 passes through the tube lens 13 and reaches the image sensor 14. The image sensor 14 can acquire a three-dimensional fluorescence image of a hologram having an interference fringe pattern with an equal inclination angle by self-interference of the fluorescence signal light. The arithmetic unit 15 calculates a three-dimensional map 30 which is three-dimensional fluorescence distribution information of a plurality of stimulation objects 10 by using a hologram of an interference fringe pattern having an equal inclination angle.

Further, the three-dimensional light stimulation holographic optical system B causes the stimulation light emitted from the laser light source 21 to enter the spatial light phase modulator 22, and the transmitted light is transmitted through the objective lens 23, the beam splitter 17, and through the objective lens 11 to be irradiated on the stimulated object 10. The spatial light phase modulator 22 is controlled by the control unit 25 so that a pattern of the light stimulation hologram is formed based on the three-dimensional map 30 calculated by the three-dimensional imaging holographic optical system A. Since the laser beam transmitted through the spatial light phase modulator 22 on which the pattern of the hologram for light stimulation is formed spatially forms a plurality of light spots by self-interference, the light spots are formed at the three-dimensional positions of the plurality of stimulation objects 10 and stimulation is given to a plurality of stimulation objects 10 simultaneously.

Figure 7:
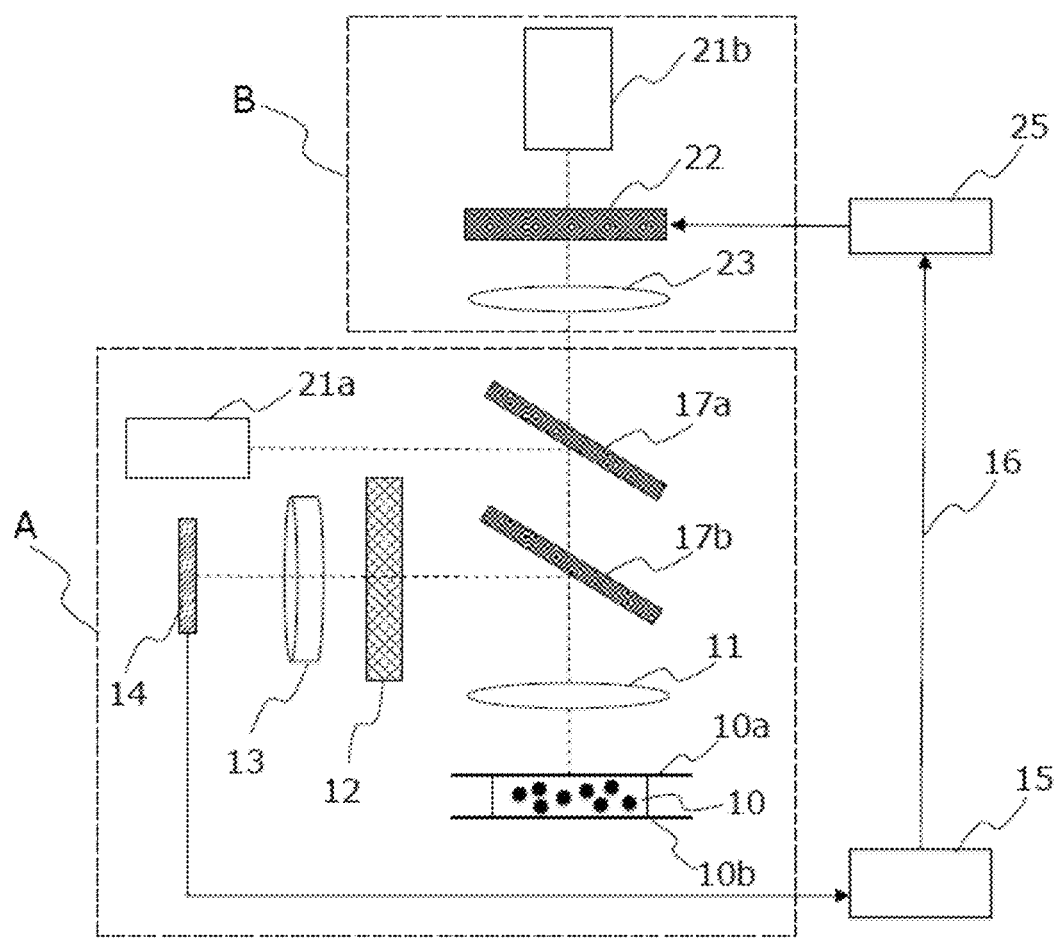
FIG. 7 shows a configuration diagram of another embodiment of the holographic three-dimensional multi-spot light stimulation device in Embodiment 2.

FIG. 7 shows a modification example of the holographic three-dimensional multi-spot light stimulation device of this Embodiment, namely, a configuration using two laser light sources (21a, 21b) that are the laser light source 21a of the three-dimensional imaging holographic optical system A and the laser light source 21b of the three-dimensional light stimulation holographic optical system B. The laser light source 21a emits fluorescence excitation light, which is reflected by the beam splitter 17a, passes through the beam splitter 17b, passes through the objective lens 11, and irradiates the stimulation object 10. Then, the fluorescence signal light of the stimulation object 10 passes through the objective lens 11, reflects off the beam splitter 17b, passes through the spatial light phase modulator 12, passes through the tube lens 13, and reaches the image sensor 14.

On the other hand, the laser light source 21b emits stimulating light having the same or different wavelength as the fluorescence excitation light, then transmits off the beam splitter 17a and the beam splitter 17b, passes through the objective lens 11, and irradiates the stimulation object 10. The beam splitter 17a reflects the fluorescence excitation light emitted from the laser light source 21a and transmits the stimulation light emitted from the laser light source 21b. Further, the beam splitter 17b transmits the fluorescence excitation light emitted from the laser light source 21a and the stimulation light emitted from the laser light source 21b, but reflects the fluorescence signal light emitted from the stimulation object 10.

Embodiment 3

Figure 8:
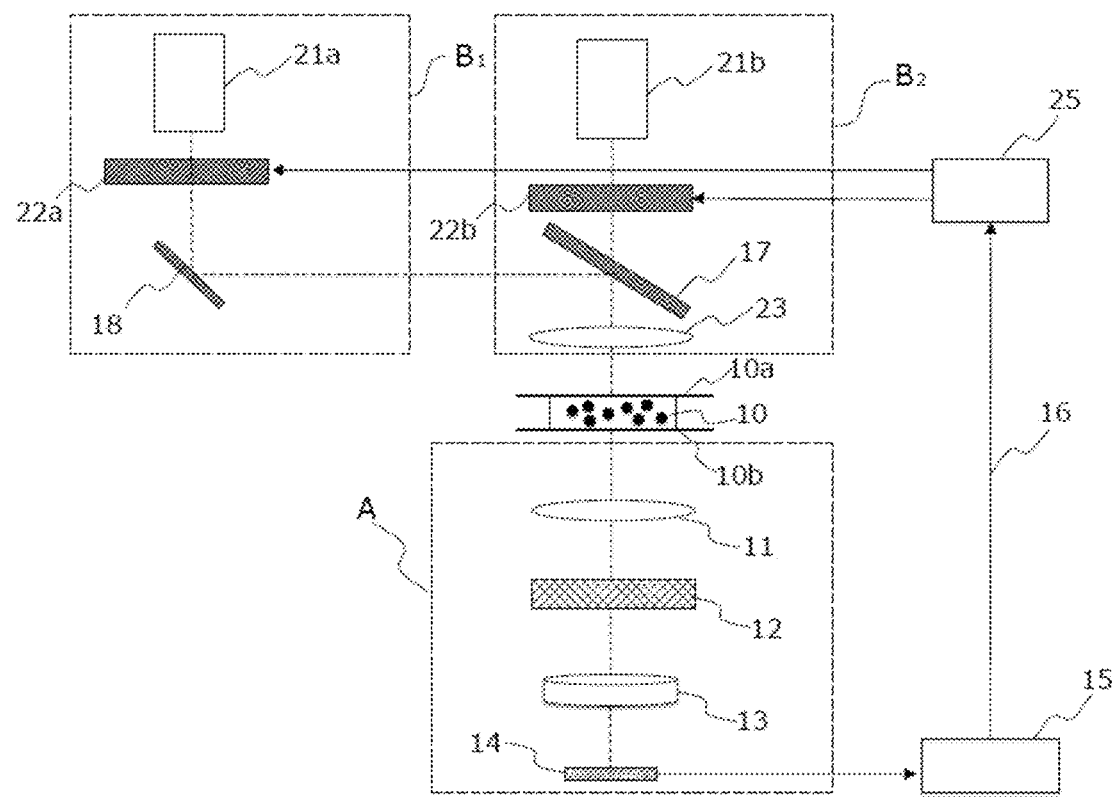
FIG. 8 shows a configuration diagram of a holographic three-dimensional multi-spot light stimulation device in Embodiment 3.

FIG. 8 shows a configuration diagram of another Embodiment of the holographic three-dimensional multi-spot light stimulation device. The holographic three-dimensional multi-spot light stimulation device shown in FIG. 8 includes a three-dimensional imaging holographic optical system A and a three-dimensional light stimulation holographic optical system B, as in the apparatus of the Embodiment 1 described above, and although the three-dimensional imaging holographic optical system A plays a role of processing the fluorescence signal light of the stimulus object 10 on the opposite side (transmission side) against the incidence side, in the apparatus of Embodiment 1, single-wavelength light (irradiation light by one laser light source 21) is used as modulated light by the optical stimulation hologram of the three-dimensional light stimulation holographic optical system B, whereas in the Embodiment here, a plurality of systems of a laser light source and a spatial light phase modulator in the three-dimensional light stimulation holographic optical system are formed (an optical system $B_1$ including a laser light source 21a, a spatial light phase modulator 22a and a reflector 18 and an optical system $B_2$ including a laser light source 21b, a spatial light phase modulator 22b, a beam splitter 17 and an objective lens 23) and it differs from the above described apparatus of Embodiment 1 in that a plurality of wavelengths are combined and used as stimulation light.

For example, in a case wherein the laser light source 21a emits the on-switch wavelength light of the cell group of the stimulation target, and the laser light source 21b emits the off-switch wavelength light of the cell group of the stimulation target, each light modulated by the light stimulation hologram by the spatial light phase modulator 22a and the spatial light phase modulator 22b becomes a state control light for controlling the state of the stimulation target object.

Further, when the laser light source 21a emits wavelength light that gives a stimulus to the cell group of the stimulation target object, and the laser light source 21b emits the fluorescence excitation light of the stimulation target object, the state of the cell group at an instant wherein stimulation is given can be observed.

Note that in this embodiment, the laser light source in the three-dimensional light stimulation holographic optical system and the optical system $B_1$ and the optical system $B_2$ of the spatial light phase modulator are formed. However, by further increasing the number of optical systems, it is possible to utilize the light of multiple wavelengths as stimulation light, by combining lights of a plurality of wavelengths.

Embodiment 4

Figure 9:
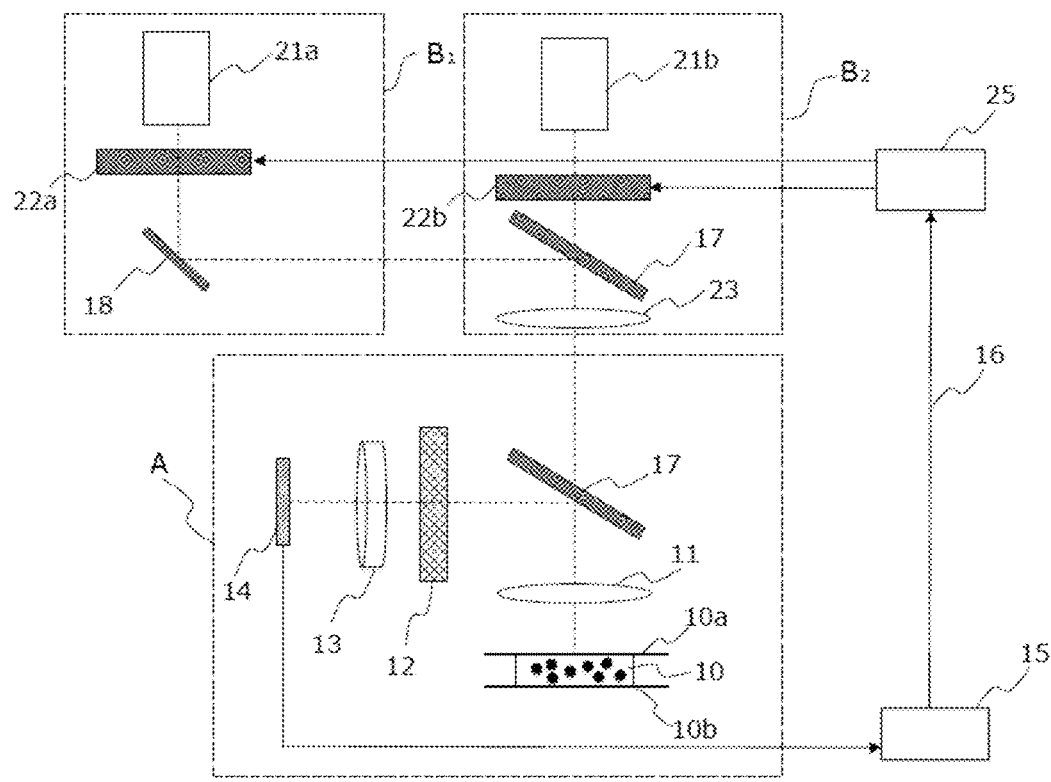
FIG. 9 shows a configuration diagram of a holographic three-dimensional multi-spot light stimulation device in Embodiment 4.

FIG. 9 shows a configuration diagram of another Embodiment of the holographic three-dimensional multi-spot light stimulation device. The holographic three-dimensional multi-spot light stimulation device shown in FIG. 9 includes a three-dimensional imaging holographic optical system A and a three-dimensional light stimulation holographic optical system B, as in the device of Embodiment 2 described above, and the three-dimensional imaging holographic optical system A is designed to process the fluorescence signal light of the stimulation object 10 on the same side as the incident side. However, in the device of Embodiment 2, light of a single wavelength (irradiation light by one laser light source 21) is used as the modulated light by the optical stimulation hologram of the three-dimensional light stimulation holographic optical system B. On the other hand, in this Embodiment, a plurality of systems of the laser light source and spatial light phase modulator are formed (laser light source 21a, the optical system $B_1$ including spatial light phase modulator 22a and the reflector 18, and the laser light source 21b, spatial light phase modulator 22b, the optical system $B_2$ including the beam splitter 17 and the objective lens 23) and lights of a plurality of wavelengths are combined to be used as the stimulating light which differs from the apparatus of the above mentioned Embodiment 2. Other aspects are similar to that of Embodiment 3 mentioned above.

Embodiment 5

Figure 10:
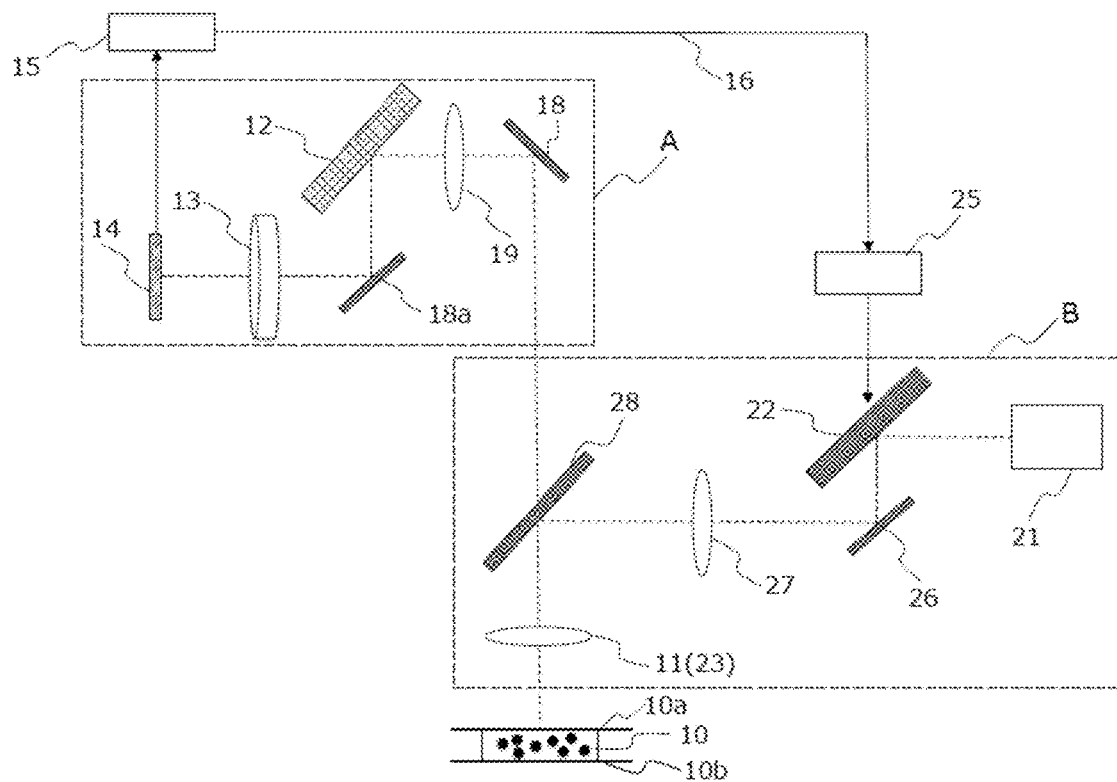
FIG. 10 shows a configuration diagram of a holographic three-dimensional multi-spot light stimulation device in Embodiment 5.
Figure 11:
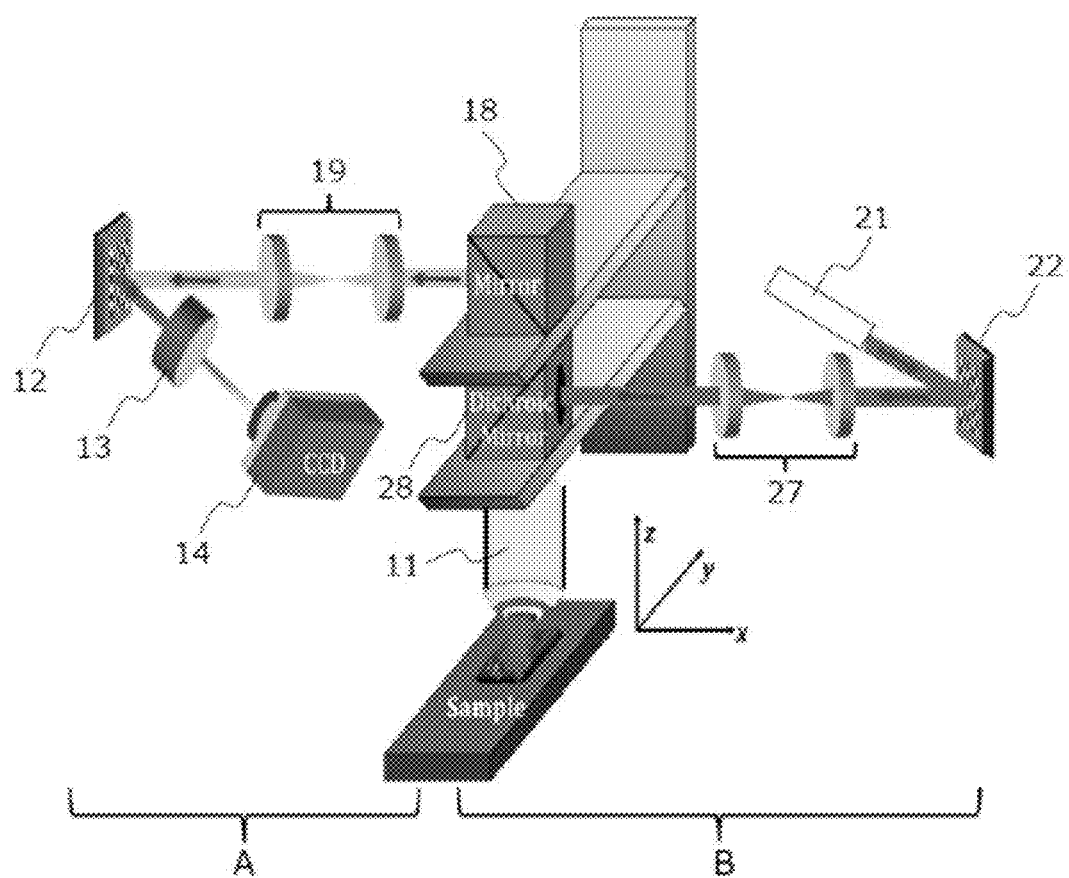
FIG. 11 shows a schematic diagram of a holographic three-dimensional multi-spot light stimulation device in Embodiment 5.

FIGS. 10 and 11 show a configuration diagram and a schematic diagram of another Embodiment of the holographic three-dimensional multi-spot light stimulation device. The holographic three-dimensional multi-spot light stimulation devices shown in FIGS. 10 and 11 include a three-dimensional imaging holographic optical system A and a three-dimensional light stimulation holographic optical system B as in the devices of Embodiments 1 and 2 described above, but the spatial light phase modulators 12 and 22 used in the respective optical systems are not transmissive but reflective, which is different from those devices as described in Embodiments 1 and 2.

In the holographic three-dimensional multi-spot light stimulation device of this Embodiment, the three-dimensional imaging holographic optical system A does not process the fluorescence signal light of the stimulation object 10 on the opposite side (transmission side) of the fluorescence excitation light as in the apparatus of Embodiment 2 but the system processes the fluorescence signal light of the stimulation target 10 on the same side as the incident side of the fluorescence excitation light.

Namely, in the three-dimensional imaging holographic optical system A shown in FIGS. 10 and 11, the fluorescence signal light emitted from the stimulation object 10 by the stimulation light (fluorescence excitation light) emitted from the laser light source 21 of the three-dimensional light stimulation holographic optical system B is directed by the objective lens 11. The light is split into parallel light, transmitted through the beam splitter 28, reflected by the reflector 18, passed through the 4f optical system 19, and incident on the spatial light phase modulator 12. The spatial light phase modulator 12 is arranged at a position where the focal plane of the objective lens 11 is in a relationship of imaging or Fourier transform. The fluorescent signal light reflected by the reflective spatial light phase modulator 12 is reflected by the reflector 18a, passes through the tube lens 13, and reaches the image sensor 14. The image sensor 14 can acquire a three-dimensional fluorescence image of a hologram having an equal inclination pattern by self-interference of the fluorescence signal light. The arithmetic unit 15 shown in the configuration diagram of FIG. 10 calculates a three-dimensional map 30 which is three-dimensional fluorescence distribution information of a plurality of stimulation objects 10 by using a hologram having a concentric pattern.

Further, in the three-dimensional light stimulation holographic optical system B shown in FIGS. 10 and 11, the stimulating light emitted from the laser light source 21 is made incident on the reflective spatial light phase modulator 22, and the reflected light is reflected by the reflecting mirror 26, and is passed through the 4f optical system 27, reflected by the beam splitter 28, and irradiated to the stimulation object 10 through the objective lens 11. As shown in the schematic diagram of FIG. 11, the spatial light phase modulator 22 is controlled by the control unit 25 so that the pattern of the light stimulation hologram is formed based on the three-dimensional map 30 calculated by the three-dimensional imaging holographic optical system A. Since the laser beam transmitted through the spatial light phase modulator 22 on which the pattern of the hologram for light stimulation is formed spatially forms a plurality of light spots by self-interference, the light spots are formed at the three-dimensional positions of the plurality of stimulation objects 10 and stimulation is given to a plurality of stimulation objects 10 at the same time.

Embodiment 6

Figure 12:
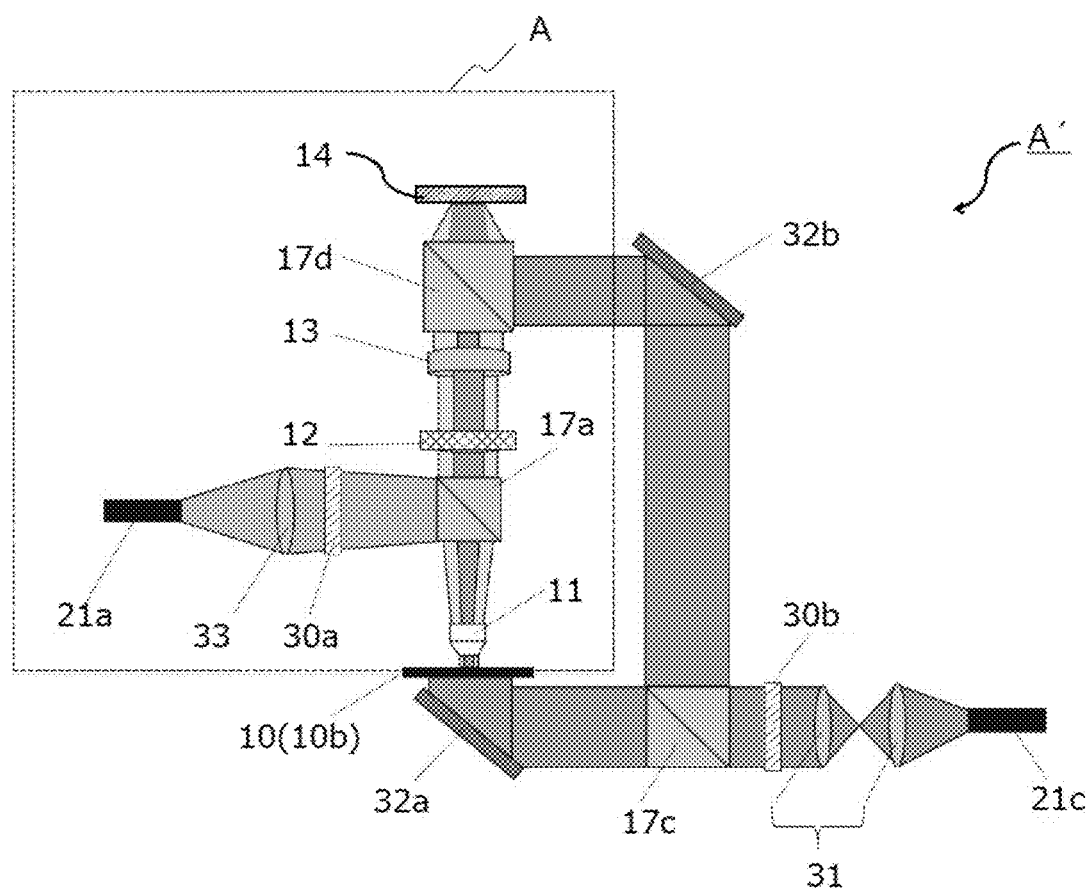
FIG. 12 shows a configuration diagram of a holographic three-dimensional multi-spot light stimulation device in Embodiment 6.

The holographic three-dimensional multi-spot light stimulation device of the embodiment shown in FIG. 12 uses two optical systems, a transmission type digital holographic microscope and a reflection type fluorescence microscope, superposed as a common optical path to the three-dimensional imaging holographic optical system A, so that 2 holograms, a phase three-dimensional image and a fluorescence three-dimensional image can be simultaneously acquired by one imaging means. Note that, as the three-dimensional light stimulation holographic optical system B, the similar optical system in any one of Embodiments 1 to 5 described above can be applied.

Hereinafter, a three-dimensional imaging holographic optical system A' that simultaneously acquires two holograms, a phase three-dimensional image and a fluorescence three-dimensional image, will be described with reference to FIG. 12.

The three-dimensional imaging holographic optical system A' shown in FIG. 12 is an image sensor in which object light and fluorescence signal light are coaxially superposed with two optical systems of a transmission type digital holographic microscope and a reflection type fluorescence microscope as a common optical path. This is a system that can simultaneously acquire two holograms, a phase three-dimensional image and a fluorescence three-dimensional image.

The stimulation object 10 on the glass plate 10b is excited by using the laser light source 21a for excitation. The excited object 10 emits fluorescence signal light having a longer wavelength than the laser light source for excitation, and the fluorescence signal light is incident on the objective lens 11 together with the laser light for excitation reflected on the surface of the glass plate 10b. Then, the beam splitter 17a sufficiently attenuates the excitation laser light, the fluorescence signal light is emphasized, and the image sensor 14 acquires a fluorescence three-dimensional image. In the three-dimensional fluorescence image, the polarization component of the fluorescence signal light self-interferes by the spatial light phase modulator 12, resulting in an interference fringe pattern having an equal inclination angle.

Also, at the same time, the laser light source 21c is used to illuminate the stimulus object 10 on the glass plate 10b. The laser light emitted from the laser light source 21c is divided into an object light path passing through the stimulation target 10 and an empty reference light path by the beam splitter 17c, respectively, and constitutes a Mach-Zehnder interferometer. The wavelength of the laser light transmitted through the stimulation object 10 is made longer than the wavelength of the excitation laser light, propagates without being affected by the beam splitter 17a, and again interferes with the reference light by the beam splitter 17d. At this time, by making a slight angle between the object light and the reference light, the image sensor 14 can acquire an off-axis hologram, that is, a hologram having an interference pattern having an equal inclination angle. The amplitude distribution and phase distribution of the object light are extracted from the obtained hologram of the interference pattern with the same inclination angle by using the Fourier transform method. In the off-axis method, the wave surface of the object light of the object 10 to be stimulated is reproduced by back-propagating to the original object position.

In the system shown in FIG. 12, the image sensor 14 can simultaneously acquire two holograms, a phase three-dimensional image and a fluorescence three-dimensional image. As described above, in the three-dimensional fluorescence image, the polarization components of the fluorescence signal light self-interfere with each other by the spatial light phase modulator 12, and the interference pattern becomes concentric or equal-inclination, while on the other hand, the phase three-dimensional image becomes an equal-inclination interference pattern. The concentric interference pattern and the equal-inclination interference pattern can be separated on the spatial frequency plane, and from the image captured by the image sensor 14, a phase hologram of a phase three-dimensional image and a fluorescence hologram of a fluorescence three-dimensional image can be separated in terms of spatial frequency plane. Even when the fluorescence hologram has an equal inclination angle, the phase and fluorescence can be separated by appropriately mapping the angle and period of the interference fringes. By providing the spatial light phase modulator 12, a ½ wavelength plate 30b is provided so that the light for the phase hologram is not affected, and the polarization of the light for the phase hologram is adjusted to a polarization state that is not affected by the spatial light phase modulator 12. Further, a ½ wavelength plate 30a is provided so that the polarization direction of the laser beam for excitation is aligned with the polarization direction in which the spatial light phase modulator 12 works.

Embodiment 7

A holographic three-dimensional multi-spot light stimulation method will be described with reference to the flow charts of FIG. 13 to FIG. 15.

Figure 13:
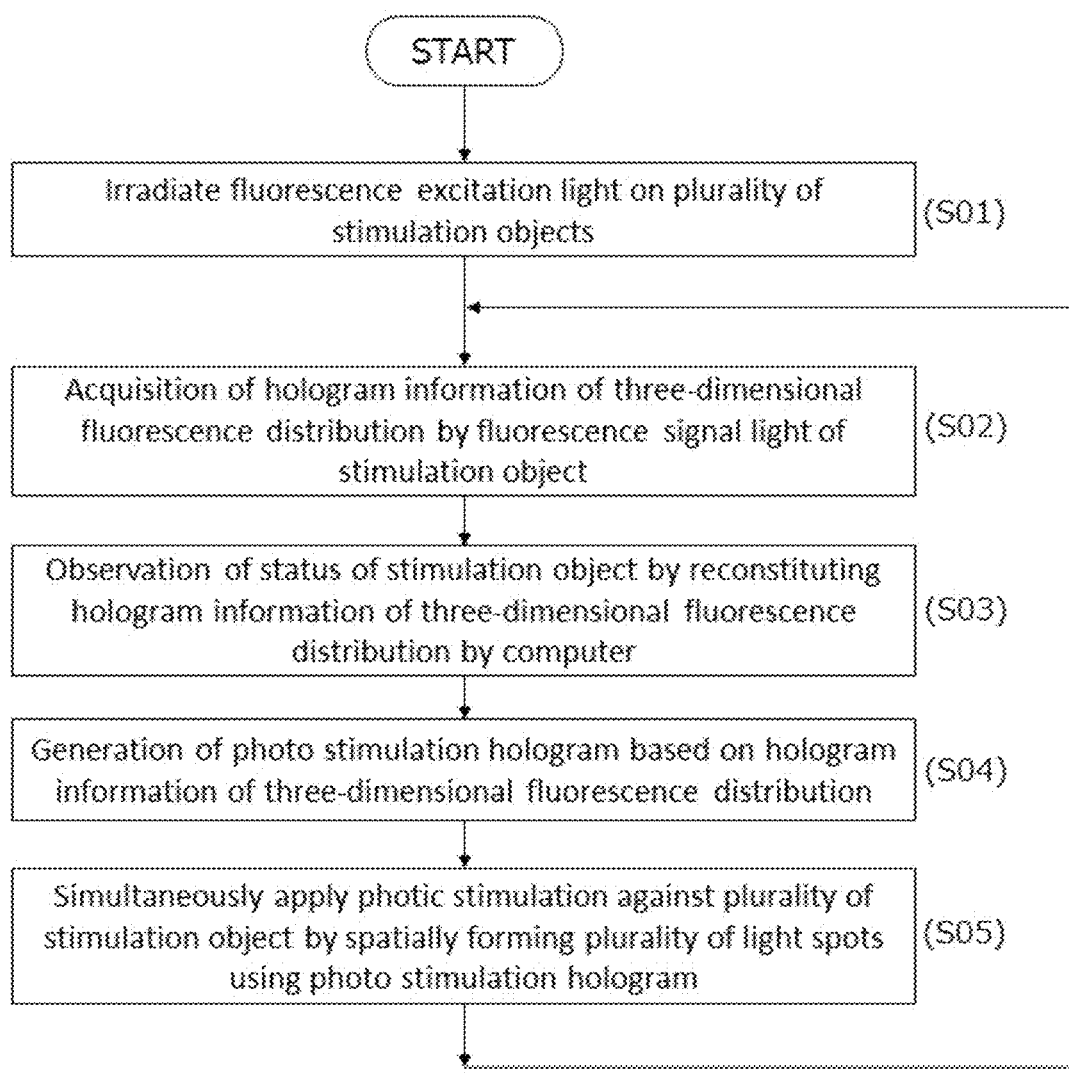
FIG. 13 shows a flow diagram of a holographic three-dimensional multi-spot light stimulation method in Embodiment 7.

As shown in the flow of FIG. 13, a holographic three-dimensional multi-spot light stimulation method of the present invention includes a step (S01) of irradiating a plurality of stimulation objects with fluorescence excitation light and a step (S02) of acquiring hologram information of a three-dimensional fluorescence distribution due to the fluorescence signal light of the stimulation objects, a step (S03) to observe the state of the object to be stimulated by reconstructing the acquired hologram information of the three-dimensional fluorescence distribution with a computer, and a step (S04) of generating a hologram for light stimulation based on the hologram information of the acquired three-dimensional fluorescence distribution, and a step (S05) of spatially forming a plurality of light spots using the hologram for light stimulation and simultaneously applying light stimulation to a plurality of stimulation objects, going back to a step S02, the state of the stimulus object after the stimulus is applied is observed by a computer reconstructing the hologram information of the three-dimensional fluorescence distribution due to the fluorescence signal light accompanying the application of the light stimulus. In the flow chart of FIG. 13, in the first step S03, the state of the stimulus object before the stimulus is applied is observed, and in the second and subsequent repeated steps S03, the state of the stimulus object after the stimulus is applied is observed. This enables dynamic observation such as observation→light stimulation→observation→light stimulation→ . . . →light stimulation→observation.

According to this flow, observation of the three-dimensional fluorescence distribution, creation of a hologram for light stimulation based on the observation result, execution of light stimulation, and observation of changes in the state of the stimulation target such as a cell group due to the execution of light stimulation, can be performed.

Figure 14:
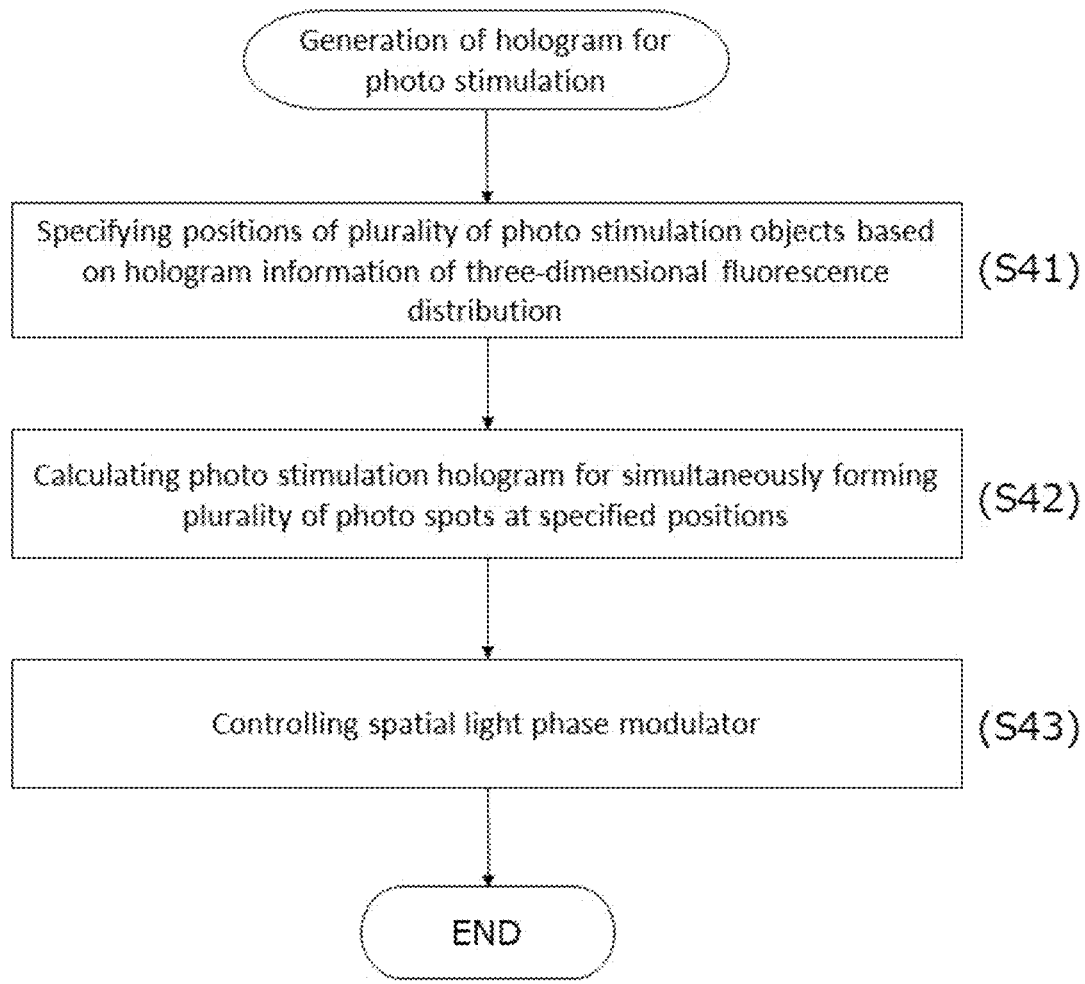
FIG. 14 shows a flow diagram of a generating process of a hologram for light stimulation.

In the step (S04) of generating the above-mentioned light stimulation hologram based on the hologram information of the three-dimensional fluorescence distribution, as specifically shown in the flow of FIG. 14, the step of specifying the position of a plurality of an object (S41), the step of calculating a hologram for light stimulation for simultaneously forming a plurality of light spots at the specified position (S42), and the step of controlling the spatial light phase modulator to generate a hologram for light stimulation (S43), are provided.

Figure 15:
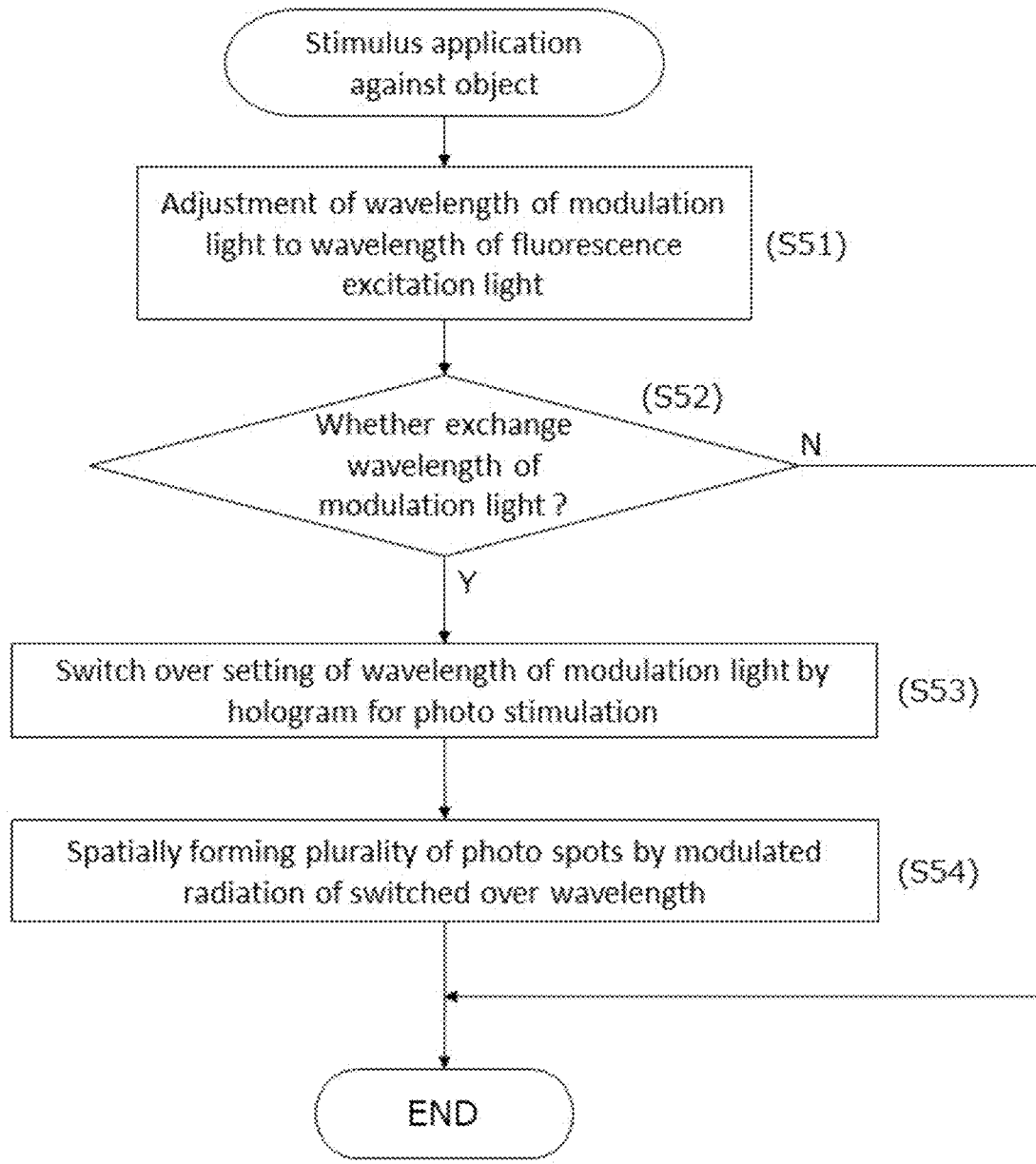
FIG. 15 shows a flow diagram of a stimulus imparting process for a stimulus target object.

And, in the step (S05) of simultaneously stimulating the stimulus object, specifically, as shown in the flow of FIG. 15, the wavelength of the modulated light is first set to the wavelength of the fluorescence excitation light (S51), the three-dimensional position of the object to be stimulated is observed, and then it is determined whether or not to switch the wavelength of the light modulated by the light stimulation hologram (S52), and if necessary, the setting of the wavelength of the modulated light is switched (S53), and a plurality of light spots are spatially formed by the modulated light of the switched wavelength (S54). By switching the wavelength of the light modulated by the light stimulation hologram, for example, in order to observe the three-dimensional position of the stimulation target, the excitation light that excites the fluorescence of the stimulation target is irradiated, and then the stimulation target is illuminated. It is possible to switch to the stimulating light for stimulating. By alternately switching the excitation light and the stimulation light, three-dimensional observation and three-dimensional stimulation can be performed with the same device. Further, by making the excitation light and the stimulation light the same, three-dimensional observation and three-dimensional stimulation can be performed at the same time.

Embodiment 8

(About Experimental Result 1)

A holographic three-dimensional multi-spot light stimulation device of the present invention has an effect of sensing the three-dimensional positions of a plurality of objects and simultaneously applying a light stimulus to a plurality of three-dimensionally located objects based on the obtained three-dimensional fluorescence distribution information. An experiment was conducted to confirm the above, and the results will be explained.

The holographic three-dimensional multi-spot light stimulation device of Embodiment 5 described above was used in the experiment. The laser light source 21 shown in FIG. 10 and FIG. 11 used a light source of a green laser (center wavelength 532 nm), and the stimulus object 10 of the sample used fluorescent beads having a diameter of 10 to 14 μm. The fluorescent beads used as the sample are excited by a green light (center wavelength 532 nm) and have the property of emitting yellow fluorescence in the range of 550 to 600 nm. Then, in order to enhance the visibility of the interference fringe related to the hologram, a bandpass filter centered on 575±12.5 nm and an Electron Multiplying CCD (EMCCD) sensor were applied, and the bandpass filter was placed in front of the EMCCD.

The three-dimensional imaging holographic optical system A image sensor 14 and spatial light phase modulator 12 are the Andor series and iXon series EMCCD sensor (1024× 1024 pixels, pixel size 13 μm) manufactured by Hamamatsu Photonics, respectively, and the reflective spatial light phase of the LCOS-SLM (Liquid Crystal on Silicon-Spatial Light Modulator) X10468 series. A modulator (600×800 pixels, 20 μm pixel pitch) was used. On the other hand, as the spatial light phase modulator 22 of the three-dimensional light stimulation holographic optical system B, a reflective spatial optical phase modulator (1920×1080 pixels, 8 μm pixel pitch, phase only) of PLUTO-2 manufactured by HOLO-EYE Photonics AG was used. As the objective lens 11 (23), a Nikon lens (50 magnification, numerical aperture NA 0.6) was used.

Figure 16:
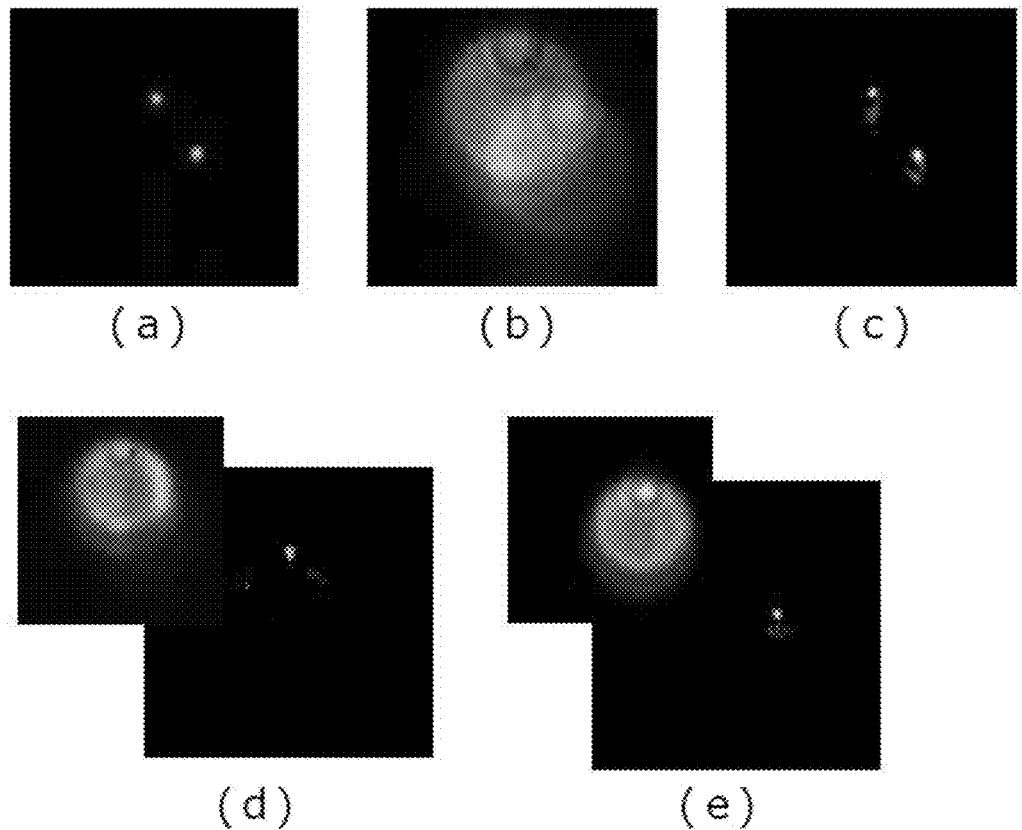
FIG. 16 shows an explanatory diagram (1) of experimental results using fluorescent beads.

Using the above apparatus, 3D imaging of fluorescent beads will be demonstrated. Further, the two fluorescent beads are placed on a glass plate and imaged by the image sensor 14 (refer to FIG. 16A). After that, the glass plate is moved by an electric moving stage by 80 μm in the z direction (depth direction) as shown in FIG. 11. If it is moved, the image obtained by the image sensor 14 will be blurred. $f_{SLM1}$=800 mm and $d_h$=300 μm are projected onto the spatial light phase modulator 12, and a hologram is recorded. The image of the interference manuscript shown in FIG. 16(b) is a recorded hologram. And then, using Fresnel propagation from the recorded hologram, it is possible to obtain a reproduced image of the reconstructed fluorescent beads by applying $z_h$=950 mm. The image shown in FIG. 16(C) is a reproduced image of the reconstructed fluorescent beads.

Next, in order for the three-dimensional light stimulation holographic optical system B to accurately irradiate each of the two beads with excitation light, it is necessary to calibrate the optical system. This calibration can be performed, for example, by recording two known pairs of light spots ($g_x$, $g_y$; h→∞) on the spatial light phase modulator 22. By comparing the two positions ($G_x$, $G_y$) and ($g_x$, $g_y$) of the focused spot, a linear relationship of spatial transformation can be obtained. Specifically, a fluorescent plate is placed on the focal point of the objective lens 11 (23) to perform calibration.

In the images shown in FIG. 16(d) and FIG. 16(e), the beads located on the upper side of FIG. 16(a) are selected and irradiated with excitation light, and the beads located on the lower side of FIG. 16(a) are selected. The respective holograms and reproduced images are shown.

The signal-to-noise ratios (SNR) of the reproduced images shown in FIGS. 16(c), (d), and (e) are 27.8, 32.2, and 33.0, respectively, and it can be seen that the signal-to-noise ratio is improved by controlling the focus of irradiation. Here, the signal-to-noise ratio is defined as the ratio of the average intensity of the signal region of the reproduced image to the average intensity of the noise region.

Figure 17:
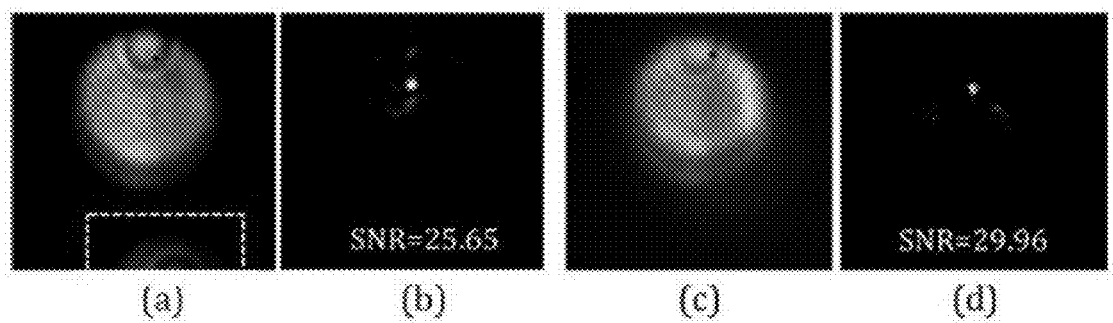

Further, a result is shown demonstrating that it is possible to irradiate a position shifted in the depth direction by a hologram. FIG. 17 shows a comparison when h→∞ and h=80 μm are applied to spatial light phase modulator 22. FIG. 17(a) and FIG. 17(b) show a hologram and a reproduced image in a state where h→∞ is applied to spatial light phase modulator 22 and there is no depth information. On the other hand, FIG. 17(c) and FIG. 17(d) show a hologram and a reproduced image in a state where h=80 μm is applied to the spatial light phase modulator 22 and there is depth information.

When h→∞ is applied and the fluorescent beads are irradiated, a hologram is observed on the upper center side as shown in FIG. 17(a), but a thin hologram is also observed on the lower part of the image surrounded by the broken line. This hologram is caused by the fact that the depth position of the light is shifted, so that the light spreads on the surface of the fluorescent beads and irradiates other fluorescent beads.

On the other hand, when depth information such as h=80 μm is applied, the hologram shown in FIG. 17(c) can be obtained. In the hologram shown in FIG. 17(c), unlike the hologram shown in FIG. 17(a), another hologram is not seen on the lower side of the image, so that the focused spot can be said to be correctly irradiated in the depth direction. In the reproduced image shown in FIG. 17(d), the SN ratio is improved as compared with the reproduced image shown in FIG. 17(b) (SN ratio: 25.65→29.96).

Figure 18:
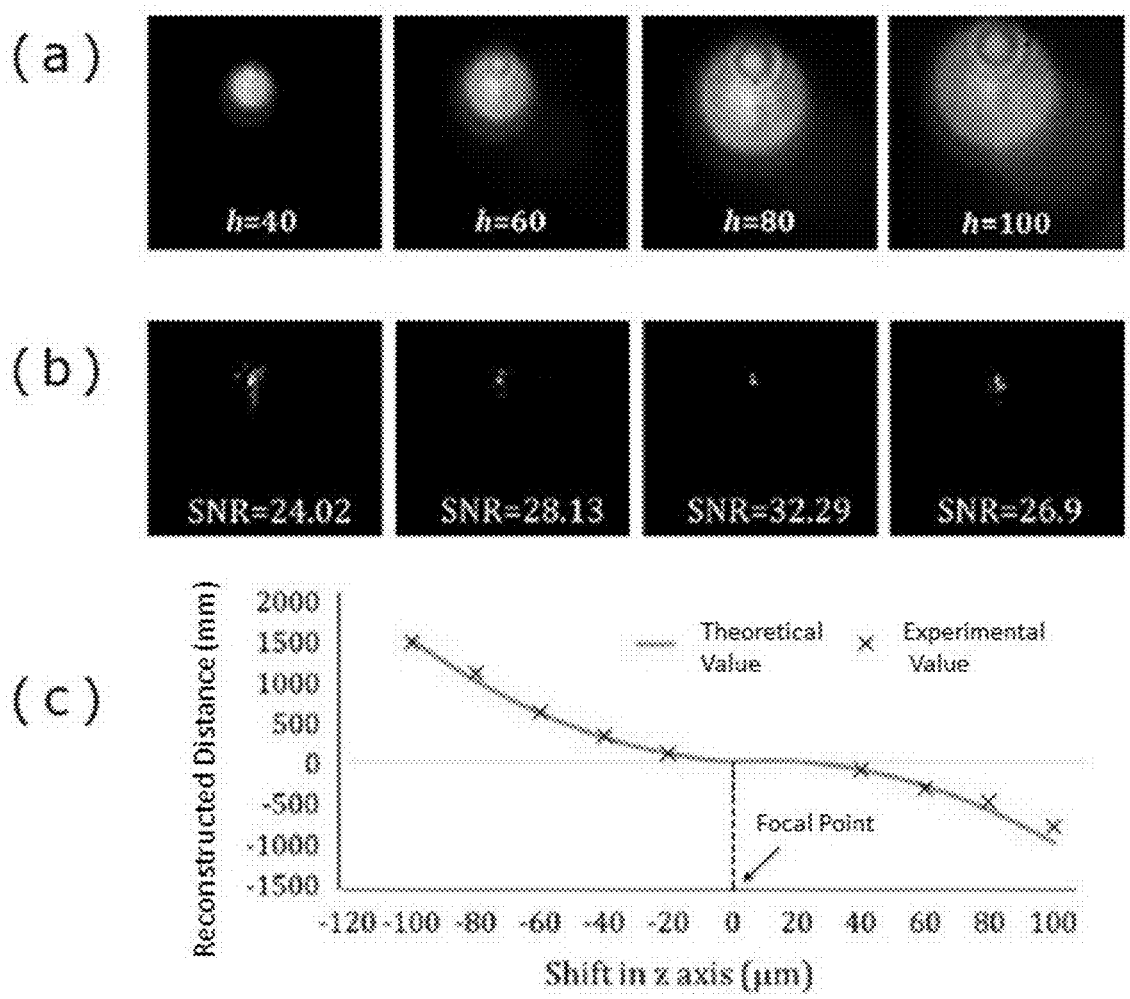

This experiment was repeated on spatial light phase modulator 22 with four more different depth informations (40, 60, 80, 100 μm). The hologram in which the experimental results are recorded and the reproduced image obtained corresponding to the hologram are shown in FIG. 18(a) and FIG. 18(b), respectively. Further, in FIG. 18(C), it can be confirmed that the reconstruction distance from the focal plane and the depth position are well matched between the experimental and the theoretical calculations.

Embodiment 9

(About Experimental Result 2)

Figure 20:
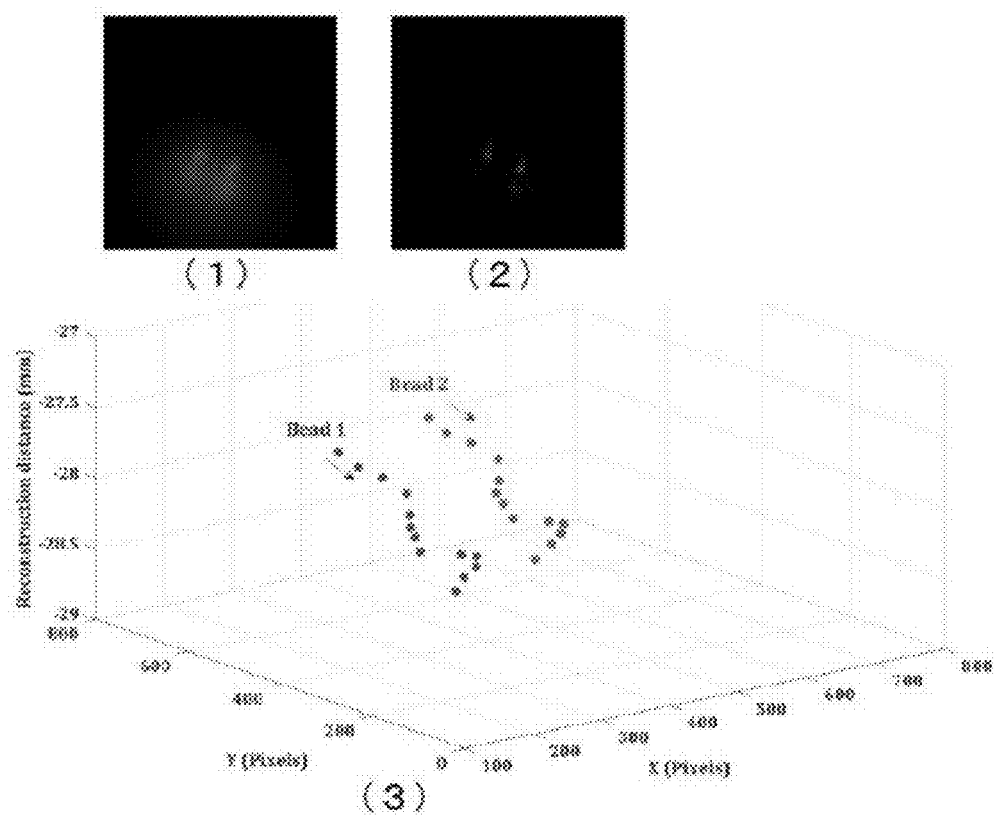
FIG. 20 shows an explanatory diagram of experimental results of video recording and playback of floating beads.

Using the apparatus shown in the above Embodiment, it has been demonstrated that three-dimensional imaging of fluorescent beads floating in water can be video-recorded and reproduced. In the images shown in FIG. 20(1) and FIG. 20(2), the beads located on the left side of FIG. 20(1) are selected and irradiated with excitation light, and the beads located on the right side of FIG. 20(1) are selected on which the excitation light was irradiated, with the respective holograms and reproduced images are shown. FIG. 20(3) shows a moving motion of these two beads recorded as a moving image, reproduced and imaged, and the three-dimensional position of the reproduced image with the passage of time is measured and plotted. The moving image is 15 frames/second, and it was confirmed that the trajectory of the three-dimensional movement of the 2 floating beads can be measured by the moving image shooting function.

Embodiment 10

(About Experimental Result 3)

Next, the results of performing the same experiment as above on human lung cancer cells (NCI-H2228 ATCC® CRL-5935™) will be described. The nuclei of human lung cancer cells as samples were stained with propidium iodide (PI) (manufactured by Thermo Fisher Scientific, P1304MP) and used. A 532 nm laser light source was used as the excitation light. The fluorescence of human lung cancer cells has a peak intensity at 620 nm. A bandpass filter in the range of 650±12.5 nm was used. The experimental results are shown in FIG. 19.

FIG. 19(a) is a fluorescence image of a large number of human lung cancer cells, and FIG. 19(b) is an image in which only one human lung cancer cell is selected and irradiated with excitation light to fluoresce. FIG. 19(c) shows the fluorescence from the nucleus of one human lung cancer cell of FIG. 19(b) recorded as a hologram, and FIG. 19(d) shows a reproduced image obtained from the hologram of FIG. 19(c). Further, an image in which two human lung cancer cells are selected and irradiated with excitation light to fluoresce is shown in FIG. 19(e), and fluorescence from the nuclei of the two human lung cancer cells in FIG. 19(e) is recorded as a hologram in FIGS. 19(f), and 19(g) is the reproduced image obtained from the hologram of FIG. 19(f).

Figure 19:
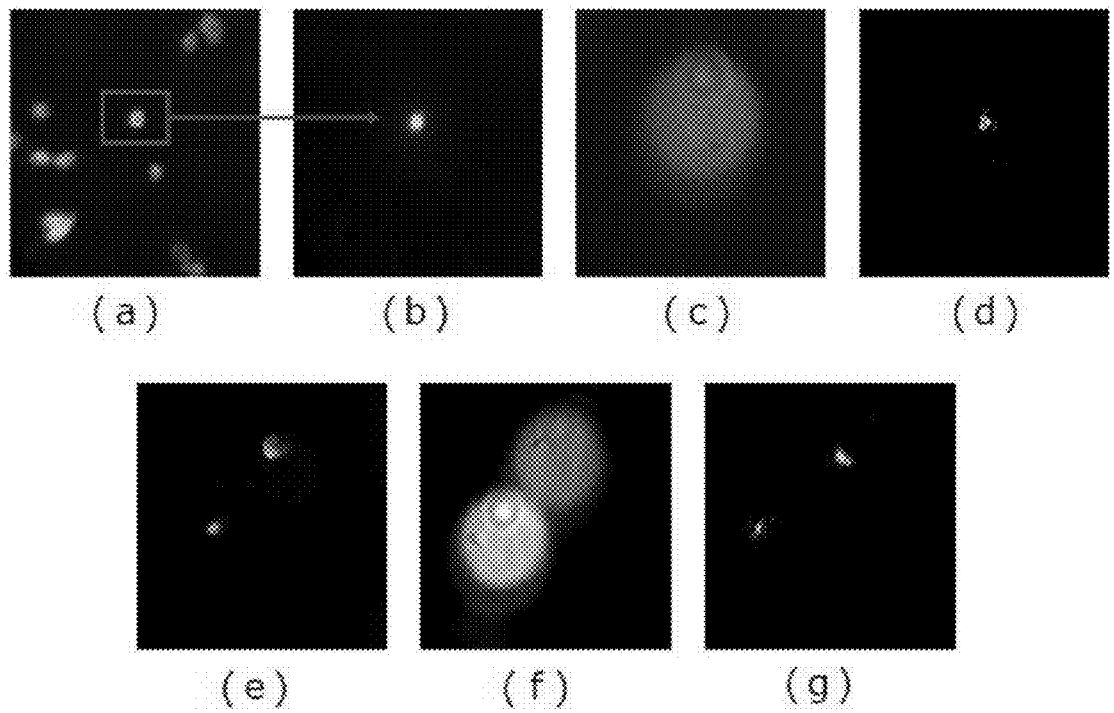
FIG. 19 shows an explanatory diagram of experimental results using human lung cancer cells.

From the results shown in FIG. 19, it was confirmed that the fluorescence from the nucleus of human lung cancer cells could be recorded as a hologram, and a reproduced image could be obtained from the recorded hologram. The human lung cancer cell has a defocus of 80 μm (a state in which the image plane of the optical system is displaced in the optical axis direction) at a position in the axial direction of the optical system.

Embodiment 11

(About Experimental Result 4)

Next, the results of performing the same experiment as above on the cells of *Physcomitrella patens* will be described. The cell nucleus of *Physcomitrella patens* as a sample was stained with fluorescent protein, irradiated with a laser light source as excitation light to fluoresce, and the fluorescence of the cell nucleus of *Physcomitrella patens* was observed using a bandpass filter. The experimental results are shown in FIG. 21.

Figure 21:
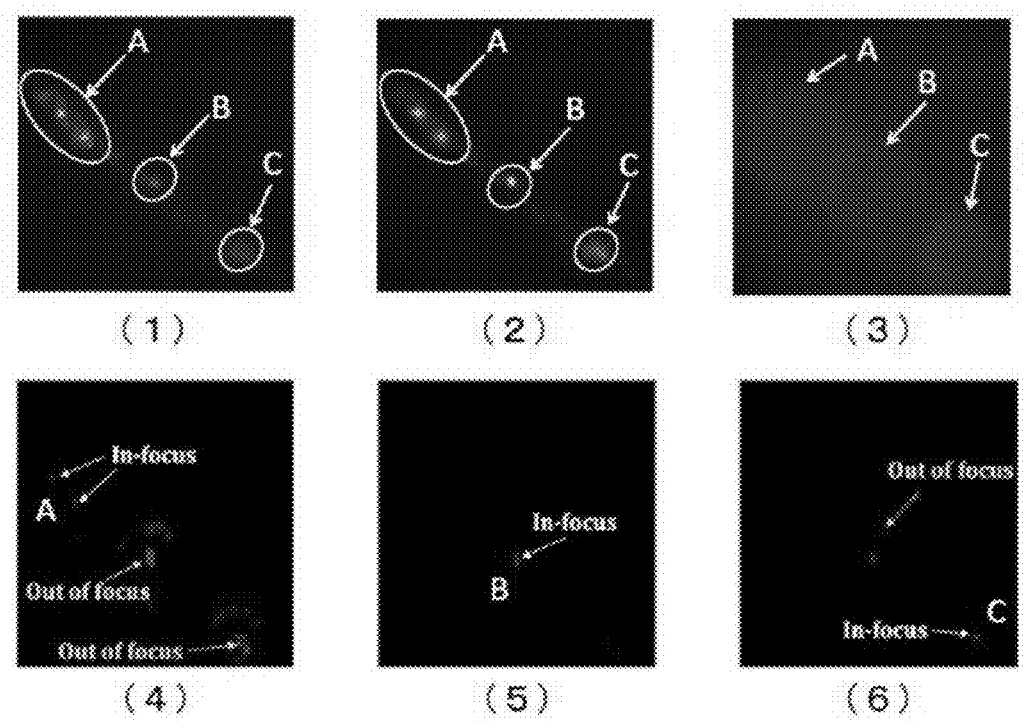
FIG. 21 shows an explanatory diagram of experimental results using cells of *Physcomitrella patens*.

FIG. 21(1) and FIG. 21(2) are fluorescence images of the cell nuclei of a plurality of *Physcomitrella patens*, and from FIG. 21(1) and FIG. 21(2), the cell nuclei of A to C can be observed fluorescently. In FIG. 21(1), the fluorescence of the two cell nuclei of A is strongly and clearly observed, whereas in FIG. 21(2), the fluorescence of the cell nucleus of B is strongly and clearly observed. Further, in both FIG. 21(1) and FIG. 21(2), the fluorescence of the cell nucleus of C is blurred and spread. Due to the varying depth of the *Physcomitrella patens* cell nuclei, some cell nuclei are strongly fluorescent and clearly observed, while others are not.

FIG. 21(3) is a hologram of fluorescence from the cell nuclei of the plurality of *Physcomitrella patens* in FIG. 21(1) and FIG. 21(2). The reproduced images obtained from the holograms A to C of FIG. 21(3) are FIGS. 21(4) to 21(6). It was confirmed that the fluorescence from the cell nuclei of a plurality of *Physcomitrella patens* could be recorded as a hologram, and that the three reproduced images shown in FIG. 21(4) to FIG. 21(6) could be obtained from the recorded hologram. The three regenerated images shown in FIG. 21(4) to FIG. 21(6) mean that there are three depths of regenerated planes in the case of the cell nucleus of *Physcomitrella patens* used in this experiment. The hologram shown in FIG. 21(3) is taken at a position shifted by 40 μm from the focal plane. The three reproduced images shown in FIGS. 21(4) to 21(6) are processed to obtain a complex amplitude distribution, and then light wave propagation calculation is performed to obtain a reproduced image. The propagation distances are 320 mm, 660 mm and 940 mm, respectively. The reason why the propagation distance is large is that it is magnified by a microscope, and when converted to the distance in the object space, it becomes 40 μm, 60 μm, and 75 μm. From the three reproduced images shown in FIGS. 21(4) to 21(6), it can be seen that the cell nuclei A to C stained with the fluorescent protein are present at positions 40 μm, 60 μm, and 75 μm away from the focal plane, respectively.

It can be seen that it is possible to stimulate a stimulation object such as a plurality of cells, positioned in 3D space by 3D imaging the object to be stimulated in advance by digital holographic technology using common optical path type off-axis incoherent light and designing an accurate multi-beam with hologram. In the present invention, it is possible to observe the state of the stimulated object after stimulation with the same device. For example, simultaneous three-dimensional observation and stimulation of biological cells can be expected to be used as a powerful tool in the field of biogenetics, especially for optogenetics. This was verified by experiments using the above-mentioned fluorescent beads and human lung cancer cells and *Physcomitrella patens* cells, which confirmed a regenerated image even when the stimulated object moved along the optical axis of the camera.

In particular, the present invention has the potential to construct an artificial neural network in mammalian animals. That is, hundreds of neurons need to be stimulated to build an effective neural network, and several milliseconds of time resolution are required to resemble the propagation of neuron signals. These can be achieved by using a spatial light phase modulator with high accuracy and fast response.

INDUSTRIAL APPLICABILITY

The present invention is useful as a microscope in the field of bioimaging. This is because it is possible to measure the shape change of cells and the movement of cell nuclei in real time, and perform programmable photostimulation on cells distributed three-dimensionally at the same time or with a time lag.

DESCRIPTION OF SYMBOLS

10 Stimulation target
10a Cover glass
10b Glass plate
11, 23 Objective lens
12, 22, 22a, 22b Spatial light phase modulator
13 Tube lens
14 Image sensor
15 Arithmetic unit
16 Data communication
17, 17a~17d, 28 Beam splitter
18, 18a, 26, 32a, 32b Reflector
19, 27, 31 4f optical system
21, 21a~21c Laser light source
25 Control unit 30 Three-dimensional map
30a, 30b ½ wave plate
31a~31e Fluorescence position
A, A' Three-dimensional imaging holographic optical system
B, B₁, B₂ Three-dimensional light stimulation holographic optical system

The invention claimed is:

1. A holographic three-dimensional multi-spot light stimulator device comprising:
   a three-dimensional imaging holographic optical system configured to employ fluorescent exciting light to acquire three-dimensional fluorescence distribution information as a self-interfering hologram resulting from fluorescent signal light from a plurality of stimulation target objects; and
   a three-dimensional light stimulation holographic optical system configured to employ a light stimulation hologram which is generated on the basis of the acquired three-dimensional fluorescence distribution information to form a plurality of light spots in space, and to impart stimulation simultaneously to the plurality of stimulation target objects; and
   wherein the three-dimensional light stimulation holographic optical system includes a first spatial light modulator and a control unit;
   wherein the control unit is configured to identify the positions of the stimulation target objects based on the three-dimensional fluorescence distribution information with the same or substantially the same spatial resolution and three-dimensional observation range as the three-dimensional imaging holographic optical system, and to calculate the light stimulation hologram for forming a plurality of light spots simultaneously at the positions of the stimulation target objects and to generate the light stimulation hologram by controlling the first spatial light modulator.

2. The holographic three-dimensional multi-spot light stimulator device according to claim 1, wherein the three-dimensional light stimulation holographic optical system includes a second spatial light modulator, a polarization-dependent bifocal lens, a polarization-dependent bifocal lens with a diffraction grating, or a volumetric holographic optical element, the fluorescence signal light is self-interfered to acquire three-dimensional fluorescence distribution information using a hologram of an interference fringe pattern having an equal inclination angle, and these are repeated; and
   wherein the control unit in the three-dimensional light stimulation holographic optical system is configured to identify the positions of the stimulation target objects within a range of ±100 μm from a depth focal position based on the three-dimensional fluorescence distribution information, and to calculate the light stimulation hologram for forming light spots simultaneously at the positions of the stimulation target objects and to generate the hologram by controlling the first spatial light modulator.

3. The holographic three-dimensional multi-spot light stimulator device according to claim 1, wherein the first spatial light modulator comprises at least one of the following: a phase modulation type spatial light modulator, or an amplitude modulation type spatial light modulator.

4. The holographic three-dimensional multi-spot light stimulator device according to claim 1, wherein the three-dimensional light stimulation holographic optical system is configured to use a plurality of wavelengths of the modulated light.

5. The holographic three-dimensional multi-spot light stimulator device according to claim 4, wherein the three-dimensional light stimulation holographic optical system is configured to use at least one of the following:
   a plurality of wavelengths of the modulated light at the same time; or
   a plurality of wavelengths of the modulated light by switching between wavelengths.

6. The holographic three-dimensional multi-spot light stimulator device according to claim 1, wherein the three-dimensional light stimulation holographic optical system is configured to use a modulated state control light for controlling a state of at least one of the stimulation target objects.

7. The holographic three-dimensional multi-spot light stimulator device according to claim 1, wherein the three-dimensional light stimulation holographic optical system is configured to use a modulated fluorescence excitation light.

8. The holographic three-dimensional multi-spot light stimulator device according to claim 1, wherein the three-dimensional imaging holographic optical system comprises at least one of the following: a second spatial light modulator, a polarization-dependent bifocal lens, a polarization-dependent bifocal lens with a diffraction grating, or a volumetric holographic optical element.

9. The holographic three-dimensional multi-spot light stimulator device according to claim 1, further comprising a holographic optical system configured for phase imaging.

10. The holographic three-dimensional multi-spot light stimulator device according to claim 1, further comprising a holographic optical system configured for acquisition of a phase three-dimensional image of at least one stimulation target object by interference light obtained by superimposing an object light passed through the stimulation target object and a reference light not passed through the stimulation target object.

11. The holographic three-dimensional multi-spot light stimulator device according to claim 1, wherein both the three-dimensional imaging holographic optical system and the three-dimensional light stimulation holographic optical system are reflective optical systems.

12. A holographic three-dimensional multi-spot light stimulator method comprising:
   irradiating a plurality of stimulation objects with fluorescence excitation light;
   acquiring hologram information of a three-dimensional fluorescence distribution using a self-interfering fluorescence signal light of the stimulation objects;
   reconstructing the acquired hologram information of the three-dimensional fluorescence distribution with a computer, thereby facilitating observation of a state of at least one stimulation object;
   generating a hologram for light stimulation that simultaneously forms a plurality of light spots at the positions of a plurality of stimulation target objects identified with the same or substantially the same spatial resolution and three-dimensional observation range as the acquired hologram of the three-dimensional fluorescence distribution;
   controlling a spatial light modulator with respect to the pattern of the hologram for light stimulation;

spatially forming a plurality of light spots using the hologram for light stimulation and simultaneously applying light stimulation to a plurality of the stimulation target objects; and after applying light stimulation to the plurality of the stimulation target objects, reconstructing the acquired hologram information of the three-dimensional fluorescence distribution with a computer, thereby facilitating observation of a state of at least one stimulation object after application of light stimulation.

13. The method according to claim 12, wherein generating a hologram for light stimulation comprises:

specifying respective positions of the plurality of stimulation objects based on the hologram information of the three-dimensional fluorescence distribution; and calculating the hologram for light stimulation for spatially forming the plurality of light spots simultaneously at specified positions.

14. The method according to claim 12, wherein simultaneously applying light stimulation to a plurality of the stimulation target objects comprises using a plurality of wavelengths of light modulated at the same time by the hologram for light stimulation.

15. The method according to claim 12, wherein simultaneously applying light stimulation to a plurality of the stimulation target objects comprises switching between light wavelengths.

16. The method according to claim 12, comprising modulating a fluorescence excitation light by using the hologram for light stimulation.

17. The method according to claim 12, comprising modulating a state control light by using the hologram for light stimulation.

18. The method according to claim 12, wherein the stimulation target objects include a group of cells, and the method comprises spatially forming the plurality of light spots using the hologram for light stimulation of cells and simultaneously applying light stimulation to a plurality of cells.

* * * * *